(12) United States Patent
Casal et al.

(10) Patent No.: US 6,284,196 B1
(45) Date of Patent: Sep. 4, 2001

(54) APPARATUS FOR MONITOR AND CONTROL OF AN AMMOXIDATION REACTOR WITH A FOURIER TRANSFORM INFRARED SPECTROMETER

(75) Inventors: Hector L. Casal, Shaker Heights, OH (US); Nazaneen Asker, Brisbane (AU); Michael J. Seely, Twinsburg, OH (US); Linda L. Nero, Columbia Station, OH (US); Jean A. Baldwin, Cleveland Heights, OH (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/282,934

(22) Filed: Apr. 1, 1999

(51) Int. Cl.$^7$ ........................................... G06F 15/46
(52) U.S. Cl. ........................ 422/62; 436/55; 436/52; 422/116; 422/82
(58) Field of Search .............. 436/52, 55; 210/656; 422/62, 116, 82; 208/72, 75, 49; 558/319, 315

(56) References Cited

U.S. PATENT DOCUMENTS

| | | |
|---|---|---|
| 2,904,580 | 9/1959 | Idol, Jr. . |
| 3,642,930 | 2/1972 | Grasselli et al. . |
| 3,936,360 | 2/1976 | Chih Wu . |
| 3,961,896 | 6/1976 | Dunn ........................................ 23/232 |

(List continued on next page.)

OTHER PUBLICATIONS

Research Focus "New Catalysts for Acrylonitrile", James Brazdil, Review, Jul./Aug. 1997.
Bomem—Industrial Software CAAP Manual (Continuous Automated Analysis Program), SPU18G, Version 1.20, Nov. 1991.
Bomem—The Michelson Series FT–IR Spectrometer User's Guide, M&MB Series Hardware, Bomem Easy Software, Version 1.50, Nov. 1992.

*Primary Examiner*—Jill Warden
*Assistant Examiner*—Brian Sines
(74) *Attorney, Agent, or Firm*—Thomas E. Nemo; Patrick J. Kim

(57) ABSTRACT

The present invention is a method and an apparatus for identifying and quantifying components in an effluent stream from an ammoxidation reactor, the apparatus comprising a microprocessor; and a Fourier Transform infrared spectrometer having a sample cell through which may flow a portion of the effluent stream, an infrared source to emit infrared radiation and pass the infrared radiation through the effluent stream, an infrared detector to detect transmitted infrared radiation at the selected infrared wavelengths and to generate absorbance data due to absorbance of the infrared radiation by the components, wherein each of the components absorbs infrared radiation at one or more of the infrared wavelengths, and an output apparatus to provide the absorbance data to the microprocessor; wherein the microprocessor is programmed to identify and quantify each of the plurality of components based upon the absorbance data and calibration data, the calibration data being obtained from recovery run analyses and calibration analyses in the sample cell. The method may be applied to utilize the apparatus to provide real-time control of the operation of an ammoxidation reactor, based on the analytical results obtained by the FT-IR spectrometer and the calibration model developed therefor.

10 Claims, 26 Drawing Sheets

U.S. PATENT DOCUMENTS

| | | | |
|---|---|---|---|
| 4,488,239 | * 12/1984 | Agarwal | 364/500 |
| 4,491,924 | * 1/1985 | Agarwal | 364/500 |
| 4,543,245 | * 9/1985 | Peterman et al. | 423/574 R |
| 4,600,541 | 7/1986 | Aoki et al. | 558/321 |
| 4,633,083 | * 12/1986 | Knorr et al. | 250/282 |
| 4,746,641 | 5/1988 | Guttmann et al. . | |
| 4,746,753 | 5/1988 | Brazdil, Jr. et al. . | |
| 4,749,469 | * 6/1988 | Beerbaum | 208/72 |
| 4,783,545 | 11/1988 | Glaeser et al. . | |
| 4,788,317 | 11/1988 | Guttmann et al. . | |
| 4,897,504 | 1/1990 | Glaeser et al. . | |
| 4,940,900 | 7/1990 | Lambert . | |
| 5,082,985 | 1/1992 | Crouzet et al. . | |
| 5,093,299 | 3/1992 | Suresh et al. . | |
| 5,235,088 | 8/1993 | Paparizos et al. . | |
| 5,262,961 | * 11/1993 | Farone | 364/500 |
| 5,380,485 | * 1/1995 | Takahashi et al. | 422/62 |
| 5,403,552 | * 4/1995 | Pardikes | 422/62 |
| 5,407,830 | * 4/1995 | Altman et al. . | |
| 5,447,692 | * 9/1995 | Keenan et al. | 422/116 |
| 5,452,232 | 9/1995 | Espinosa et al. . | |
| 5,475,612 | 12/1995 | Espinosa et al. . | |
| 5,490,085 | 2/1996 | Lambert et al. . | |
| 5,499,193 | * 3/1996 | Sugawara et al. | 364/500 |
| 5,538,643 | * 7/1996 | Kallos et al. | 210/656 |
| 5,576,469 | 11/1996 | Brazdil, Jr. et al. . | |
| 5,671,153 | * 9/1997 | Brinkmeyer et al. | 364/502 |
| 5,693,587 | 12/1997 | Brazdil, Jr. et al. . | |
| 5,712,797 | 1/1998 | Descales et al. . | |
| 5,740,073 | 4/1998 | Bages et al. . | |
| 5,756,802 | * 5/1998 | Li et al. | 558/319 |
| 5,763,883 | 6/1998 | Descales et al. . | |
| 5,770,757 | 6/1998 | Drenski et al. . | |
| 5,861,228 | 1/1999 | Descales et al. . | |
| 5,879,629 | * 3/1999 | Capuano et al. . | |
| 6,122,557 | * 9/2000 | Harrell et al. | 700/45 |

* cited by examiner

APPARATUS FOR MONITOR AND CONTROL OF AN AMMOXIDATION REACTOR WITH A FOURIER TRANSFORM INFRARED SPECTROMETER

TECHNICAL FIELD OF THE INVENTION

The present invention relates to identification and quantification of a plurality of components in the effluent of an ammoxidation reactor by means of Fourier Transform infrared (FT-IR) spectroscopy and use of the information thus obtained to provide control and optimization of the ammoxidation reaction.

BACKGROUND OF THE INVENTION

The present invention finds significant use in the ammoxidation of both propylene and propane to produce acrylonitrile, and in general in the ammoxidation of olefins, paraffins and other starting materials to produce the corresponding nitrites. This reaction is well known and is described, for example, in U.S. Pat. No. 3,642,930 (olefins) or U.S. Pat. No. 4,897,504 (paraffins), the disclosures of which are incorporated herein by reference. In general, the ammoxidation reaction is accomplished by contacting the reactant olefin or paraffin (or other starting material), oxygen and ammonia, in the vapor phase, with a particular ammoxidation catalyst, at an elevated temperature and at atmospheric or near atmospheric pressure. The reaction may be carried out in the same manner and under the conditions generally set forth, for example, in the '930 patent or the '504 patent.

In addition to olefins and paraffins, oxygenated hydrocarbons can be ammoxidized with the known ammoxidation catalysts. For example, alcohols such as isopropanol, n-propanol, t-butyl alcohol, and aldehydes such as acrolein and methacrolein can be readily converted to nitriles. In general, the starting materials are olefins, paraffins, aldehydes and alcohols containing three or four carbon atoms. The general ammoxidation process for converting olefins, alcohols and aldehydes to the corresponding nitriles is well known and described for example in U.S. Pat. Nos. 3,642,930 and 4,897,504, and others assigned to The Standard Oil Company.

The following description of the ammoxidation reaction, both in the background and in the description of the invention, may use an olefin, sometimes specifically propylene, for exemplary purposes. The invention is not so limited and is applicable to ammoxidation reactions using any known starting material and particularly including paraffins in addition to olefins. It is further noted that, as would be understood by a person of skill in the art, it may be necessary to adjust the process, including changing catalysts used, according to the particular starting material employed and according to the products desired to be produced. For convenience herein, the term "hydrocarbon" may be employed for referring to the organic feed material, be it olefin, paraffin or other known ammoxidation feed material.

In monitoring and controlling the ammoxidation reaction, it has heretofore been the practice in the industry to operate the reactor based on test results obtained from previous operations of the reactor, where the test results are obtained from quality control procedures known as "recovery runs". Recovery runs are laboratory chemical analyses performed on collected samples of the effluent stream and/or collected products of the ammoxidation reaction (i.e., a day's production). Recovery runs require a minimum of several hours to perform, so cannot provide contemporaneous, real-time information as to the ammoxidation reaction. For these reasons, recovery runs can only provide hindsight information as to the parameters of operation of the ammoxidation reaction. The industry has long sought both more rapid analysis of the reaction products and a way to provide such information in real time, so as to allow the control and optimization of the ammoxidation reaction during the course of a reaction, i.e., in "real-time".

SUMMARY OF THE INVENTION

In one embodiment, the present invention is an apparatus for identifying and quantifying components in an effluent stream from an ammoxidation reactor, comprising a microprocessor; and a FT-IR spectrometer having a sample cell through which may flow a portion of the effluent stream, an infrared source to emit infrared radiation and pass the infrared radiation through the effluent stream, an infrared detector to detect transmitted infrared radiation at selected infrared wavelengths and to generate absorbance data due to absorbance of the infrared radiation by the components, wherein each of the components absorbs infrared radiation at one or more of the infrared wavelengths, and an output apparatus to provide the absorbance data to the microprocessor; wherein the microprocessor is programmed to identify and quantify each of the plurality of components based upon the absorbance data and calibration data, the calibration data being obtained from recovery run analyses and FT-IR calibration analyses in the sample cell.

In one embodiment, the invention is a method for identifying and quantifying components in an effluent stream from an ammoxidation reactor, comprising (A) advancing a portion of the effluent stream through a sample cell in a FT-IR spectrometer; (B) scanning the portion in the sample cell with infrared energy at a plurality of infrared wavelengths, wherein each of the components absorbs the infrared energy at one or more of the plurality of selected wavelengths; (C) detecting the infrared radiation passing through the sample cell and generating absorbance data for each of the components; and (D) quantifying each of the components by comparing the absorbance data to a calibration curve for each component in a microprocessor programmed to quantify each of the components.

In one embodiment, the invention is a method for controlling operation of an ammoxidation reactor based upon real-time quantitative analysis of components in an effluent stream from the ammoxidation reactor, comprising (a) preparing a calibration curve for each of the components by analyzing a plurality of effluent streams each containing the plurality of components by a calibration process comprising: (a-1) advancing at least a portion of each effluent stream through a sample cell in a FT-IR spectrometer; (a-2) scanning the effluent stream advancing through the sample cell with infrared energy across a range of infrared wavelengths and obtaining absorbance data at selected wavelengths across the range of infrared wavelengths; (a-3) collecting at least one sample corresponding to each effluent stream; (a-4) performing a recovery run analysis on the at least one sample to obtain quantitative data for each of the components in each sample; and (a-5) determining the calibration curve for each of the components by correlating the absorbance data and the quantitative data; (b) obtaining real-time absorbance data for each of the components in an operational effluent from the ammoxidation reactor by performing steps (a-1) and (a-2) thereon and calculating in a microprocessor programmed therefor real-time quantitative data for the operational effluent from the calibration curve and the real-time absorbance data; and (c) controlling the ammoxidation reactor to optimize production of at least one of the components based on the real-time quantitative data.

In one embodiment, the ammoxidation reactor is operated so as to produce acrylonitrile. In one embodiment, the acrylonitrile is produced from a propylene feed. In one embodiment, the acrylonitrile is produced from a propane feed. While the following description particularly describes the invention as applied to an acrylonitrile reactor, it is to be understood that this is for illustrative purposes only, and the invention, applicable broadly to ammoxidation reactors, is not so limited.

Thus, the present invention provides the real-time information needed to allow improved control and immediate, on-going optimization of the reaction in an ammoxidation reactor during occurrence of the reaction for which the information is obtained, thus providing the long sought "real-time" analyses and process control.

DETAILED DESCRIPTION

Figure 1:
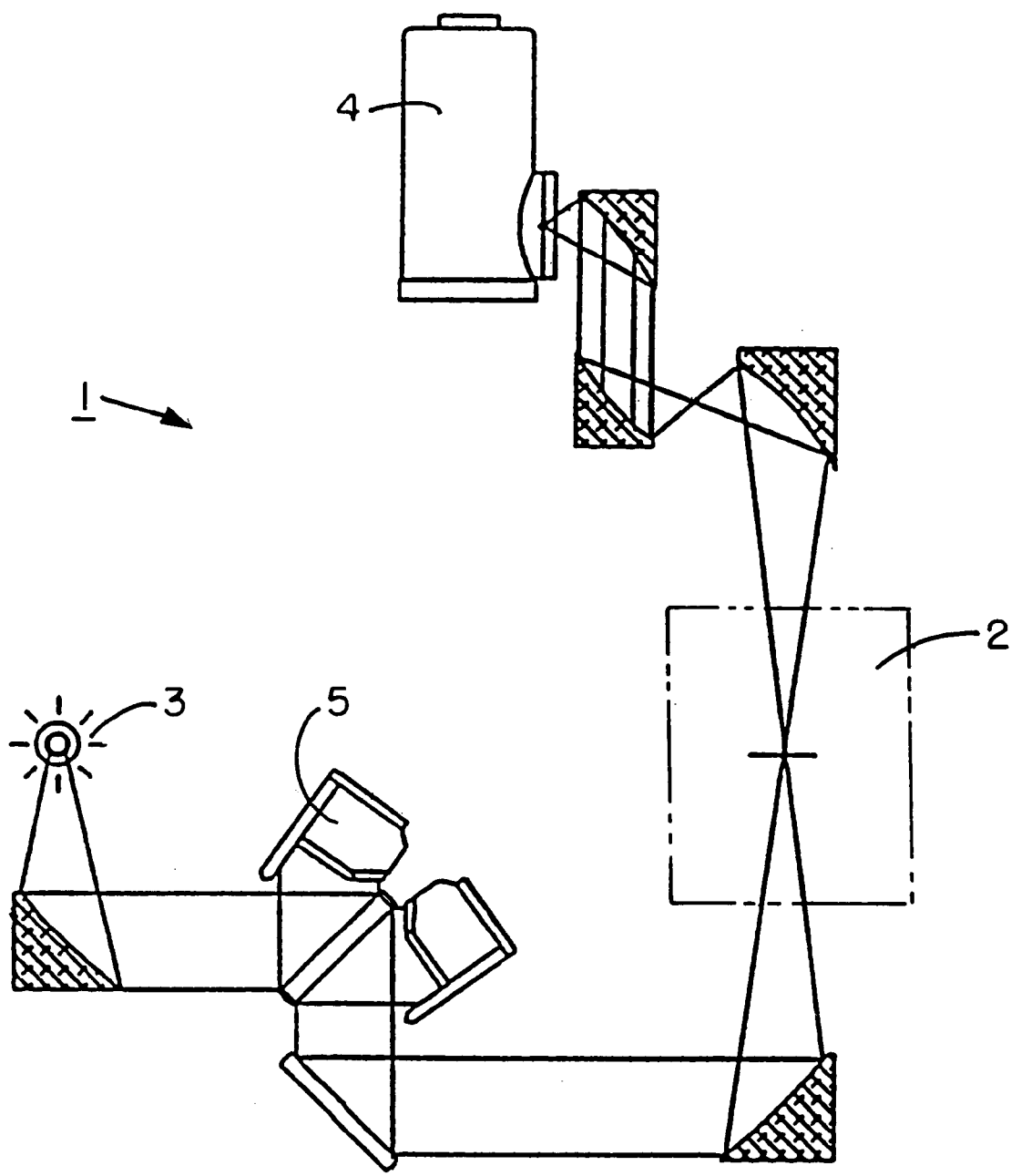
FIG. 1 is a schematic diagram of the optics portion of an FT-IR spectrometer.

Fourier Transform Infrared (FT-IR) spectroscopy uses energy in the form of infrared (IR) radiation, which is between the visible and microwave regions of the electromagnetic spectrum. FIG. 1 is a schematic diagram of the optics portion of a FT-IR spectrometer 1 such as that used to obtain IR spectra of the combined effluent of an acrylonitrile reactor in accordance with the present invention. The FT-IR spectrometer 1 shown in FIG. 1 schematically represents, in one embodiment, a BOMEM Michelson FT-IR spectrometer, which includes a Michelson interferometer. In the FT-IR spectrometer a sample to be analyzed is placed in or passed through a FT-IR sample cell 2 which is specially designed to transmit light at infrared (IR) wavelengths. IR radiation generated by a broad-spectrum IR source 3 passes through the sample cell 2, and travels on to a sensitive IR detector 4. The IR radiation from the source 3 is split by an interferometer 5 such that the IR radiation follows paths having slightly different pathlengths through the sample cell 2 and to the IR detector 4. The different pathlengths correspond to different wavelengths of the IR radiation. Some wavelengths of the IR radiation may be absorbed by the sample, indicating the presence of particular molecular bonds by the presence of characteristic adsorption bands. The detector 4 generates a signal based on changes in the relative intensities of the IR radiation arriving at the detector 4 by the two different paths, one of which passes through the FT-IR sample cell 2, as it scans through a spectrum of IR radiation. A computer performs a Fourier transform to convert the time-modulated intensity changes into a spectrum of absorption vs. wavelength for the sample. The instrument produces a graph of absorption against wavelength of radiation called an IR spectrum. Analysis of the characteristic spectral absorption bands allows identification of the composition of the sample. The signal used to generate the graph also may be sent to a memory device in a microprocessor for calculation of numerical results. The sample cell 2 in FIG. 1 is shown in phantom since its actual dimensions and position may vary widely depending upon its arrangement with respect to the sample source, such as in an industrial production setting, for example, an acrylonitrile reactor.

In the present invention, the FT-IR spectral absorption bands are analyzed for a plurality of components in the effluent from an acrylonitrile reactor. However, each of the plurality of components is not separately analyzed in a pure state to identify its distinctive absorption bands. Rather, many spectra are collected on actual effluents from the acrylonitrile reactor, the corresponding recovery run analyses performed, and by use of sophisticated computer algorithms, qualitative and quantitative correlations are developed for each of a plurality of the components in the effluent stream. The actual effluents from the acrylonitrile reactor contain the combined plurality of components which will be found in later operational effluents. The relative quantities of each of the plurality of components in the effluents used for calibration are thus similar to the relative quantities of the components in the operational effluents. As a result any interferences should be similar, and be cancelled out.

As a result of the quantitative correlations, calibration curves are developed by which each of the components in the effluent from the acrylonitrile reactor may be identified and quantified. Thus, the effluent from an acrylonitrile reactor is repeatedly analyzed, and particular absorption bands unique to each of the plurality of components are identified by the computer program and correlated with the quantities of each component as provided by conventional recovery run analyses.

Details of the procedure used to obtain the calibration curves are provided in the following.

Ammoxidation Reactors and FT-IR Apparatus

Any source of oxygen may be employed in the ammoxidation reaction process. In one embodiment, air is used. In one embodiment, a mixture of oxygen and nitrogen is used. For economic reasons it is generally preferred that air be employed as the source of oxygen. In one embodiment molecular oxygen is used and gives similar results. For process control reasons, a mixture of oxygen and nitrogen, such as air, is preferred due to the more precise control obtained when controlling the flow of a larger volume of gas. In one embodiment, the molar ratio of oxygen to the hydrocarbon in the feed to the reaction vessel is in the range from about 0.5:1 to about 4:1. In one embodiment, the molar ratio is from about 1:1 to about 3:1.

The molar ratio of ammonia to hydrocarbon in the feed to the ammoxidation reactor may vary between about 0.05:1 to about 5:1. There is no real upper limit for the ammonia/hydrocarbon ratio, but there is generally no reason to exceed the 5:1 ratio. At ammonia/hydrocarbon ratios appreciably less than the stoichiometric ratio of 1:1, various amounts of oxygenated derivatives of the hydrocarbon will be formed. Within the ammonia-hydrocarbon range stated, maximum utilization of ammonia is obtained and this is highly desirable. It is generally possible to recycle any unreacted hydrocarbon and unconverted ammonia. When paraffins are used as feed the process continuously recycles both the feed paraffin and ammonia.

In one embodiment, water is included in the feed. In embodiments using fixed-bed systems, water may improve the selectivity of the reaction and the yield of nitrile. In one embodiment, the molar ratio of water to olefin is in the range from about 0.1:1 and higher. In one embodiment, the ratio is in the range from about 1:1 to about 6:1. In one embodiment, the ratio is up to about 10:1.

In one embodiment, the reaction is carried out at an elevated temperature in the range from about 200° C. to about 600° C. In one embodiment, the reaction is carried out at a temperature in the range from about 400° C. to about 55° C. In one embodiment, the reaction is carried out at a temperature in the range from about 420° C. to about 500° C. In one embodiment, the reaction is carried out at a temperature of about 420° C. In one embodiment, the reaction is carried out at pressures from about atmospheric to about 2 to 3 atmospheres. In general, high pressures, i.e. above 15 atmospheres, are not suitable since higher pressures tend to favor the formation of undesirable byproducts.

The apparent contact time is not critical, and contact times in the range of from 0.1–40 seconds may be employed. The optimal contact time will, of course, vary depending upon the reactant being used. In one embodiment, the contact time is from about 1 to about 15 seconds.

The ammoxidation reaction is generally carried out in the vapor phase. The reaction product passing out of the reactor is normally in the form of a vapor. This gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by one of a number of different techniques such as, for example, distillation or water extraction/distillation. Additional steps can be employed to separately recover HCN and/or acetonitrile from the gross reaction product. In addition, any excess ammonia may be recovered and recycled.

Figure 2:
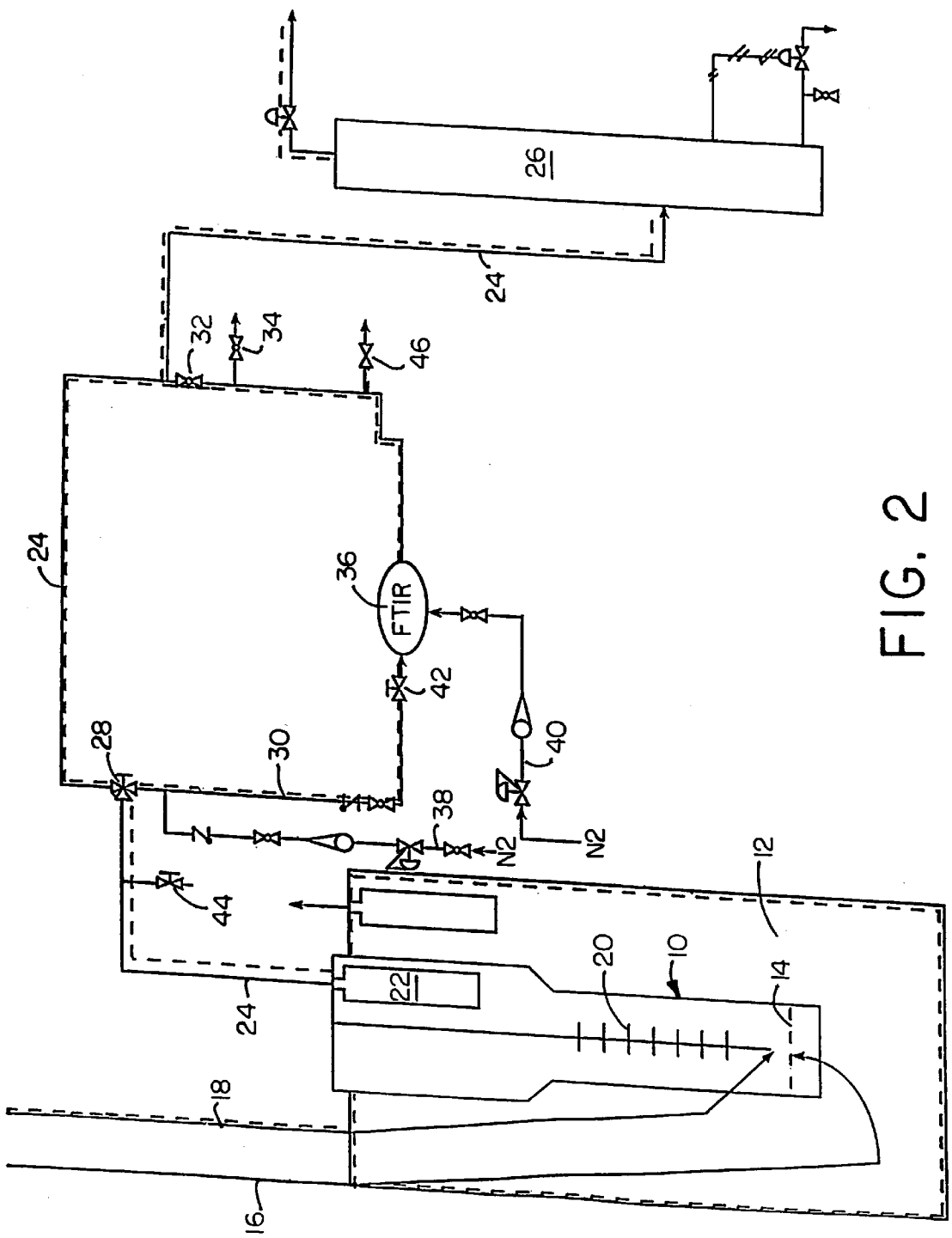
FIG. 2 is a schematic diagram of an acrylonitrile reactor and FT-IR analysis apparatus in accordance with one embodiment of the present invention.

FIG. 2 is a schematic diagram of an acrylonitrile reactor and FT-IR analysis apparatus in accordance with the present invention. It is noted that many of the process elements shown in FIG. 2 include both dashed and solid lines. Such combined dashed and solid lines indicate that these process elements are heated, and should be maintained at an elevated temperature during normal operations. Specific temperatures vary somewhat depending on the particular process element, and are provided in the following.

The apparatus shown in FIG. 2 includes an acrylonitrile reactor 10. The acrylonitrile reactor 10 shown in FIG. 2 is a pilot-scale unit. The ammoxidation reaction takes place in the acrylonitrile reactor 10. In one embodiment, the reactor is a fluid bed reactor containing solid, loose particles of catalyst. In one embodiment, the reactor 10 is a fixed bed reactor, in which the catalyst is attached to a solid, fixed support. The reactor 10 may be disposed in a mass such as sand bath 12, in order to provide a heat source for the high temperatures employed in the ammoxidation reaction. While the ammoxidation reaction is an exothermic reaction, in a pilot scale reactor such as the reactor 10 shown in FIG. 2, additional heat must be applied to maintain the reactor 10 at the desired temperature level for the reaction. The sand bath 12 is heated from an external source and is the source of heat in the pilot scale reactor 10 in addition to the heat generated by the ammoxidation reaction. The following description, while generally applicable to either a fluid or fixed bed ammoxidation reactor, is particularly directed to the fluid bed reactor. Those skilled in the art will recognize and understand the differences, and will recognize that the present invention is not limited to a particular type of ammoxidation reactor.

As shown in FIG. 2, the reactor 10 may include a baffle plate 14 in the lower portion of the reactor 10. The three feed materials, i.e., the hydrocarbon feed, ammonia and oxygen (in one embodiment in the form of air), are injected into the lower portion of the reactor 10. The air is injected via an air line 16 below the baffle plate 14. The hydrocarbon feed and ammonia are injected just above the baffle plate 14 via a heated combined feed line 18.

As shown in FIG. 2, the reactor 10 may further include a series of mixing plates 20, which ensure thorough and intimate contact between the gaseous reactants and the solid particles of catalyst in the reactor. The mixing plates 20 shown in FIG. 2 are schematic, and it is to be understood that various embodiments of mixing elements may be used. In the upper portion of the reactor 10 is a filter or strainer 22. The strainer 22 allows the gaseous products and any un-reacted gaseous reactants to pass, but prevents passage of solid materials such as the catalyst particles. In one embodiment, the strainer 22 may be a cyclone-type separator. In general, the strainer 22 is an apparatus for separating solids and gases. The interior of the reactor 10, via the strainer 22, is in fluid connection with an effluent line 24. The effluent line 24 carries the effluent from the acrylonitrile reactor to a scrubber 26, and thence to product recovery and, optionally, reactant recycling apparatus (not shown). The effluent line 24 is heated to maintain all reactor products in the gaseous state, as set forth above and shown in FIG. 2. All lines carrying effluent to the scrubber 26 should be heated, and such heating should be to a relatively constant temperature.

As shown in FIG. 2, the effluent line 24 may include a 3-way or T-connection 28 at which a side stream effluent line 30 may be split off from the primary effluent line 24. The side stream line 30 may be substantially smaller than the primary effluent line 24. The side stream line 30 is heated, as set forth above and shown in FIG. 2. The side stream line 30 also includes a shut-off valve 32 and a purge valve 34. A sample cell 36 of an FT-IR spectrometer is disposed in the side stream line 30. The sample cell 36 in FIGS. 2 and 3 corresponds to the sample cell 2 in FIG. 1. While it is possible to have the sample cell 36 disposed in the primary effluent line 24, in a commercial process this would not be preferred, due to the large volume of gaseous products exiting the ammoxidation reactor 10 (FIG. 2) or a commercial scale ammoxidation reactor 100 (FIG. 3), and the concomitant large size sample cell which would be required.

As shown in FIG. 2, first and second nitrogen purge lines 38, 40 are provided. The first nitrogen purge line 38 is provided to purge the entire side stream line 30, and is used to remove traces of the effluent prior to, e.g., service of the sample cell 36 or shutdown of the reactor system. When the 3-way valve 28 is set so that the side stream line 30 is closed off from the effluent line 24, the shut-off valve 32 is closed and the purge valve 34 is opened, nitrogen from the first nitrogen line 38 may be used to purge the entirety of the side stream line 30, including the sample cell 36. The second nitrogen purge line 40 is provided to purge only the sample cell 36, such as for calibration and background determinations. In order to purge the sample cell 36, it would be necessary to close a cell shut-off valve 42 to prevent entry of effluent from the reactor, to close the shut-off valve 32 and to open at least one purge valve, such as the purge valve 34, while passing nitrogen into and through the sample cell 36.

As shown in FIG. 2, the effluent line 24 includes a sample valve 44. The sample valve 44 may be used for removing samples for chemical analysis, such as for recovery run analysis. Alternatively, or in addition, recovery run samples may be removed from a second sample valve 46. In the recovery run analyses used for calibration of the FT-IR spectrometer in the present invention, the samples were collected from the second sample valve 46, downstream from the sample cell 36.

Figure 3:
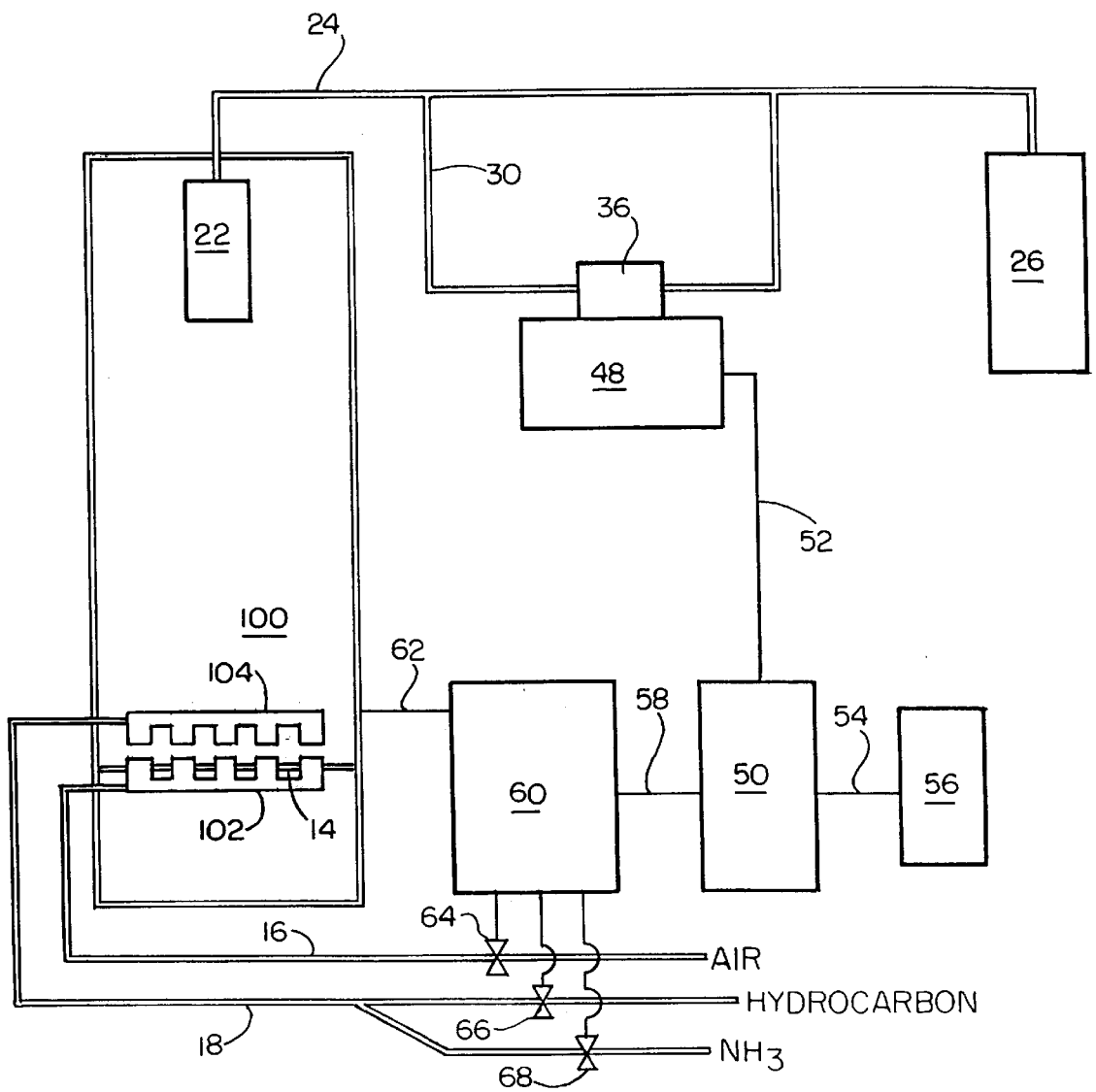
FIG. 3 is a schematic diagram of an apparatus for analyzing the effluent from an acrylonitrile reactor and providing operative control of the reactor, in accordance with one embodiment of the present invention.

FIG. 3 is a schematic diagram of an apparatus for analyzing the effluent from an acrylonitrile reactor and providing operative control of the reactor, in accordance with one embodiment of the present invention. Where the elements of FIG. 3 are the same as in FIG. 2, the same reference numbers are used, and the description thereof is omitted. For simplicity, some elements are not shown in FIG. 3.

The reactor system shown in FIG. 3 includes the commercial-scale reactor 100. The reactor 100 differs is some aspects from the reactor 10 shown in FIG. 2 and described in relation thereto. The reactor 100 does not include a sand bath as a heat source. In a commercial scale reactor, such as the reactor 100, a greater quantity of heat is generated in the exothermic ammoxidation reaction than necessary to sustain the reaction. In the reactor 100, rather than adding heat to sustain the reaction, heat must be removed to control the reaction. Thus, as will be described more fully below, controlling the temperature of the reactor 100 is generally performed by adjusting the amount of heat removed from the reactor, rather than adjusting the amount of heat added, as is the case for a smaller reactor, such as the reactor 10 shown in FIG. 2.

The reactor 100 includes a means for distributing the gaseous feed materials to the reactor. In one embodiment, the reactor 100 includes a first sparger 102 and a second sparger 104. The first sparger 102 feeds and distributes the air or other oxygen-containing feed material to the reactor 100. As shown in the embodiment of FIG. 3, the first sparger 102 may be disposed below or near the level of the baffle plate 14. The second sparger 104 feeds and distributes the ammonia and hydrocarbon feed materials to the reactor 100. As shown in the embodiment of FIG. 3, the second sparger 104 may be disposed above the level of the baffle plate and above the level of the first sparger 102. In other embodiments, other known distribution devices may be employed, such as one or more jet mixers, injectors, baffled-flow mixers, multiple nozzle-type inlets or multiple spargers.

As shown in FIG. 3, the apparatus includes an FT-IR spectrometer 48, of which the sample cell 36 is a part. The FT-IR spectrometer 48 includes optics, an IR source, and an IR detector, such as those shown in FIG. 1, and circuitry to measure the strength of the IR radiation originating from the IR source and reaching the IR detector as well as the sample cell 36. The FT-IR spectrometer 48 further includes circuitry to generate absorbance data, and an output device capable of outputting the absorbance data together with associated information such as the wavelength of IR radiation. Details of the structure and operation of an FT-IR spectrometer are known to those of skill in the art and will not be further set forth herein, except as may be needed to disclose the present invention.

As shown in FIG. 3, the FT-IR spectrometer 48 is connected to a microprocessor 50 via a FT-IR output line 52. The FT-IR spectrometer 48 outputs the absorbance data together with the associated information such as the wavelength of IR radiation, via the output line 52 to the microprocessor 50. The microprocessor 50 is linked via an input line 54 to an input device 56 by which calibration information and data, recovery run data and other information may be input to the microprocessor 50. The input device 56 may comprise a keyboard for manually inputting data, and may be linked to an additional, possibly remote, microprocessor which generates or provides calibration data. The microprocessor 50 may also be linked to other sources, such as the output from a data collection memory device. The microprocessor 50 is programmed to quantify the components in the effluent from the acrylonitrile reactor 100, based on the absorbance data provided by the FT-IR spectrometer 48, and on the calibration data provided by the input device 56.

As shown in FIG. 3, the microprocessor 50 is attached via an output line 58 to a reactor controller 60. The reactor controller 60 controls the operation of the reactor 100, communicating with the reactor 100 by a reactor control line 62. The reactor controller 60 operates a set of mass flow control valves for the reactants fed to the reactor. In one embodiment, the various control valves associated with the acrylonitrile reactor are pneumatically operated, and are actuated when the microprocessor transmits an electrical signal to a transducer which converts the electrical into a pneumatic signal. The pneumatic signal in turns opens or closes or adjusts the respective control valves in known fashion.

The mass flow control valves for the reactants include an air control valve 64, a hydrocarbon feed control valve 66 and an ammonia control valve 68. As described with respect to the air line 16 in FIG. 2, and as shown in FIG. 3, the air line 16 carries the air, the flow of which is controlled by the air control valve 64, to the reactor 100. Similarly, the combined feed line 18 carries the combined hydrocarbon and ammonia feed to the reactor 100, the flow of each controlled respectively by the hydrocarbon control valve 66 and the ammonia control valve 68.

Based on the output from the microprocessor 50, received via the input line 58, the reactor controller 60 also controls reactor conditions, such as internal reactor temperature and pressure, temperatures of the feed lines 16 and 18, and temperature of the effluent line 24, via the reactor input line 62. The reactor controller 60 controls the flow of cooling water to the reactor 100, by which the temperature of the reactor 100 is controlled. The cooling system is not shown in the drawings. The reactor conditions, the flows of the reactants and other parameters, such as the reactor temperature and the rate of addition or removal of heat, can be precisely controlled by the reactor controller 60 based on the output from the microprocessor 50 and the desired distribution of products, which may be set by, e.g., a human operator. As will be understood by those of skill in the art, the reactor controller 60 may include, e.g., a further microprocessor and input device by which a human operator can select variables to adjust and optimize production of particular products in the reactor 100.

In one embodiment, the sample cell 36 in the FT-IR spectrometer 48 used with the acrylonitrile reactor is constructed of stainless steel with ZnSe windows through which the IR passes, with the effluent from the acrylonitrile reactor passing through the interior of the sample cell 36 between the windows, thereby resulting in the IR beam passing through the effluent. In one embodiment, the pathlength in the sample cell 36 is 10 cm. The temperature in the sample cell 36 is maintained at an elevated level, as described above with respect to the effluent lines generally, in order to maintain the effluent in a uniform, gaseous state. In one embodiment, the temperature in the effluent line and the sample cell 36 is maintained at about 200° C. In one embodiment, the temperature of the line and the sample cell 36 is maintained at about 150° C. It is important that the temperature in the sample cell 36 remain constant, and that the temperature in the sample cell 36 be the same during calibrations and during production runs using the calibrations as set forth herein.

Figure 4:
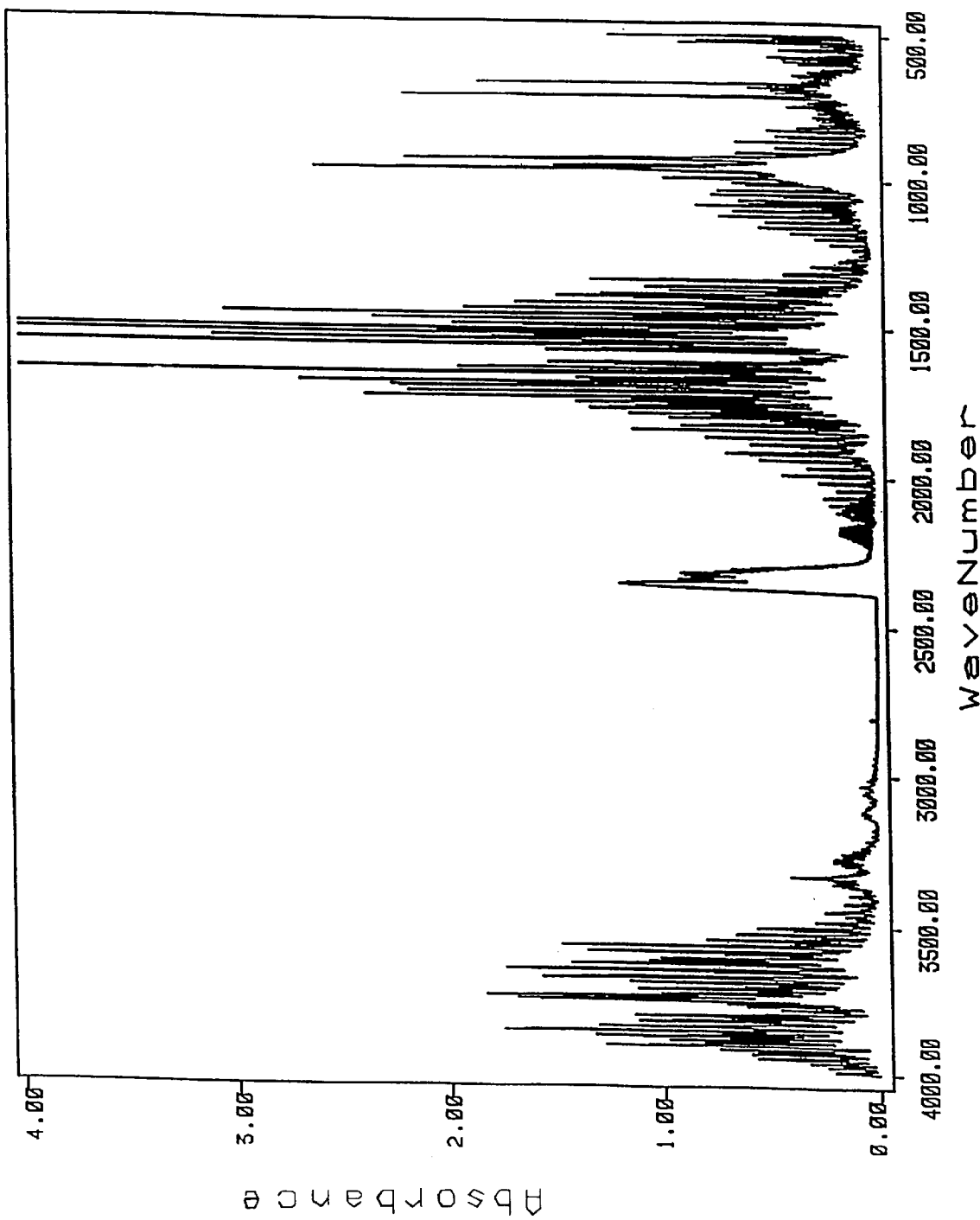
FIG. 4 is an FT-IR spectrum of an exemplary sample of an effluent from an acrylonitrile reactor.

Sample FT-IR spectra are shown in FIGS. 4 and 5A–5J. In each spectrum shown in FIGS. 4 and 5A–5J, the resolution is 1 $cm^{-1}$. FIG. 4 is an FT-IR spectrum of an exemplary combined effluent from an acrylonitrile reactor, obtained in an apparatus such as that shown schematically in FIG. 3, at 200° C. and scaled such that the largest peaks are full scale on the Y-axis. The FT-IR spectrum of FIG. 4 includes wavenumbers in the range from 500 $cm^{-1}$ to 4000 $cm^{-1}$. In the present specification, as is common in the art, in the IR region of the electromagnetic spectrum, wavelength is expressed in terms of wavenumber per centimeter, i.e., the number of waves per centimeter, or simply reciprocal centimeters, $cm^{-1}$.

Figure 5A:
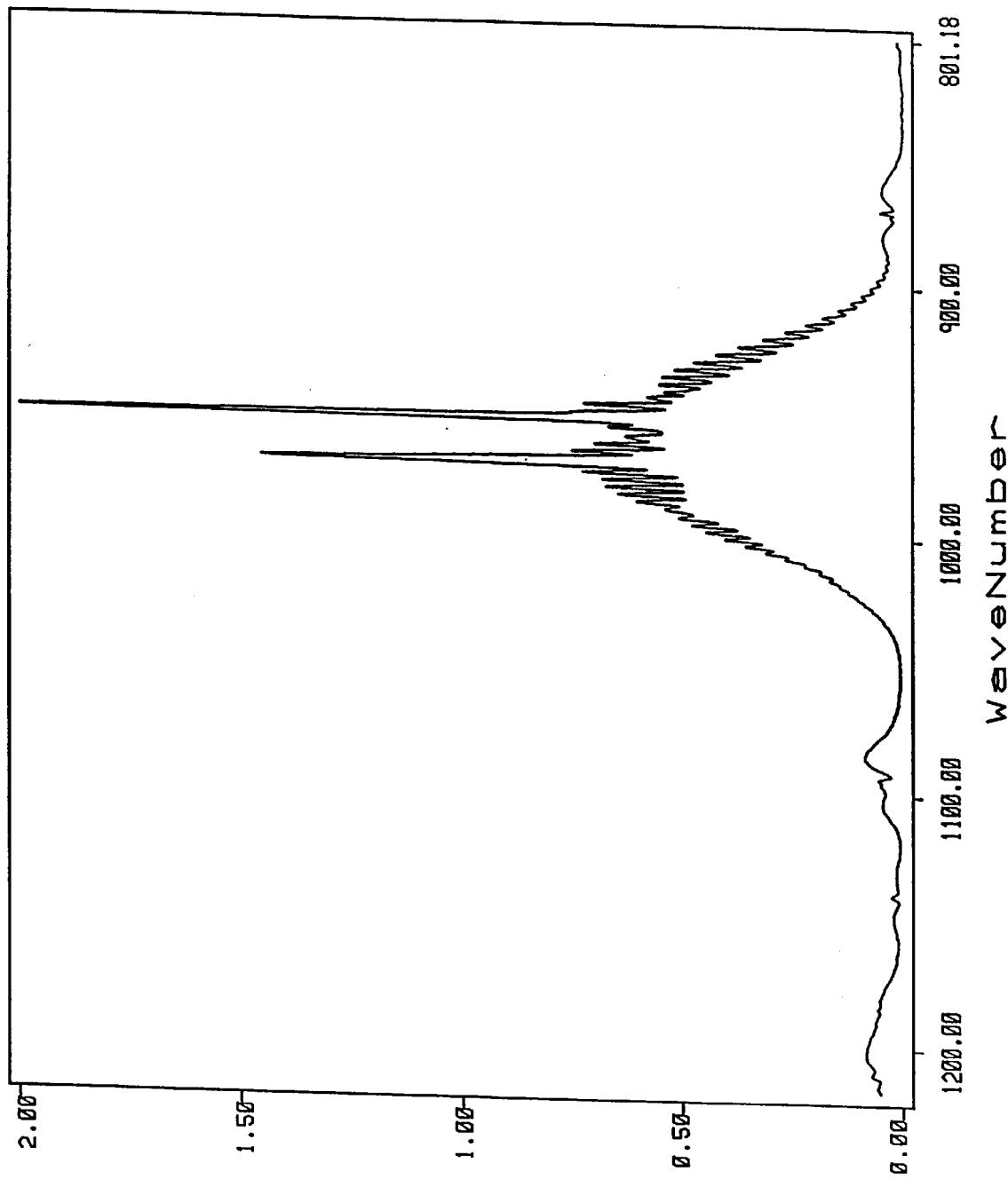
FIGS. 5A–5J are FT-IR spectra of ten individual components of an effluent of an acrylonitrile reactor in which propylene is the hydrocarbon feed, each figure showing the spectrum of an individual component.
Figure 5B:
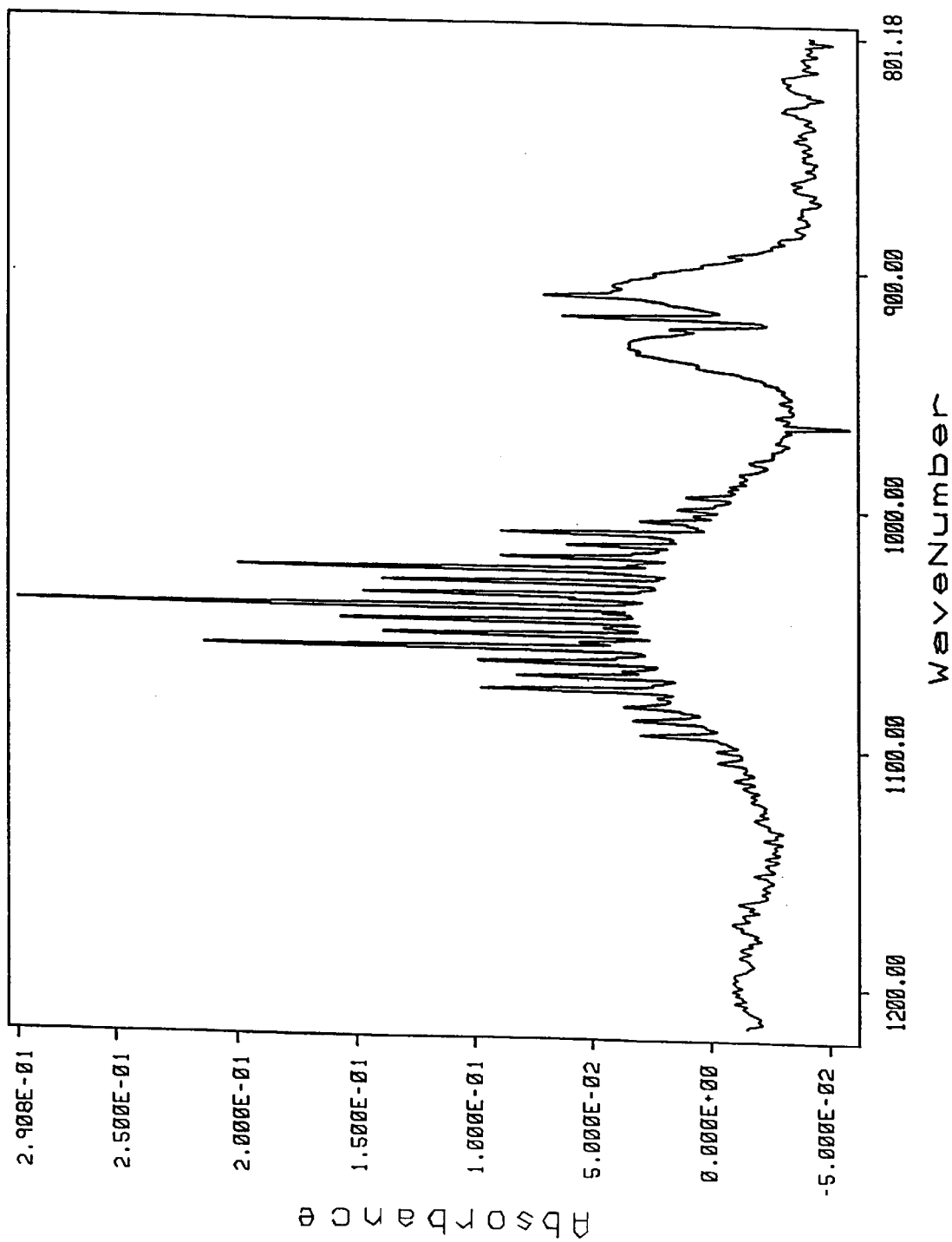
Figure 5C:
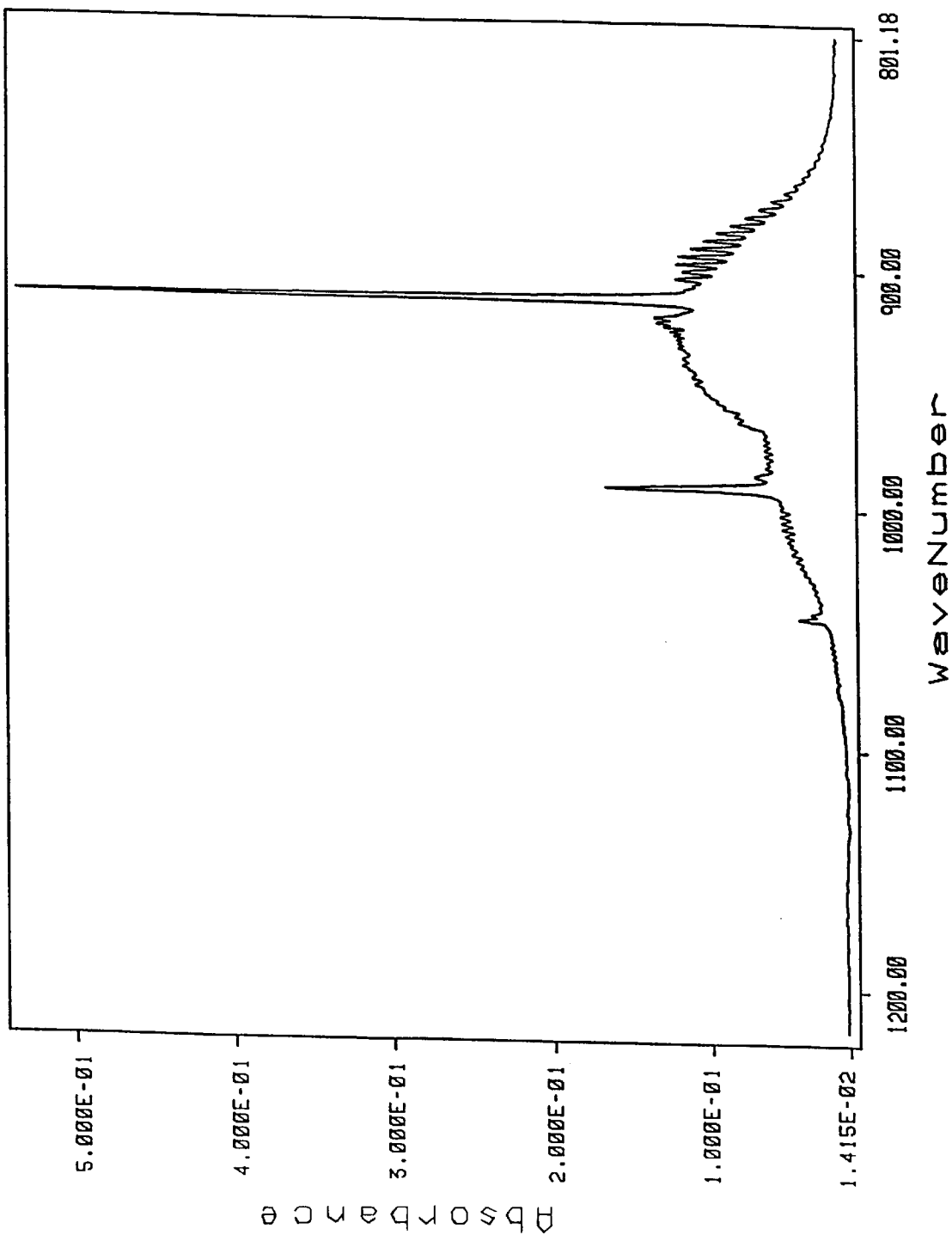
Figure 5D:
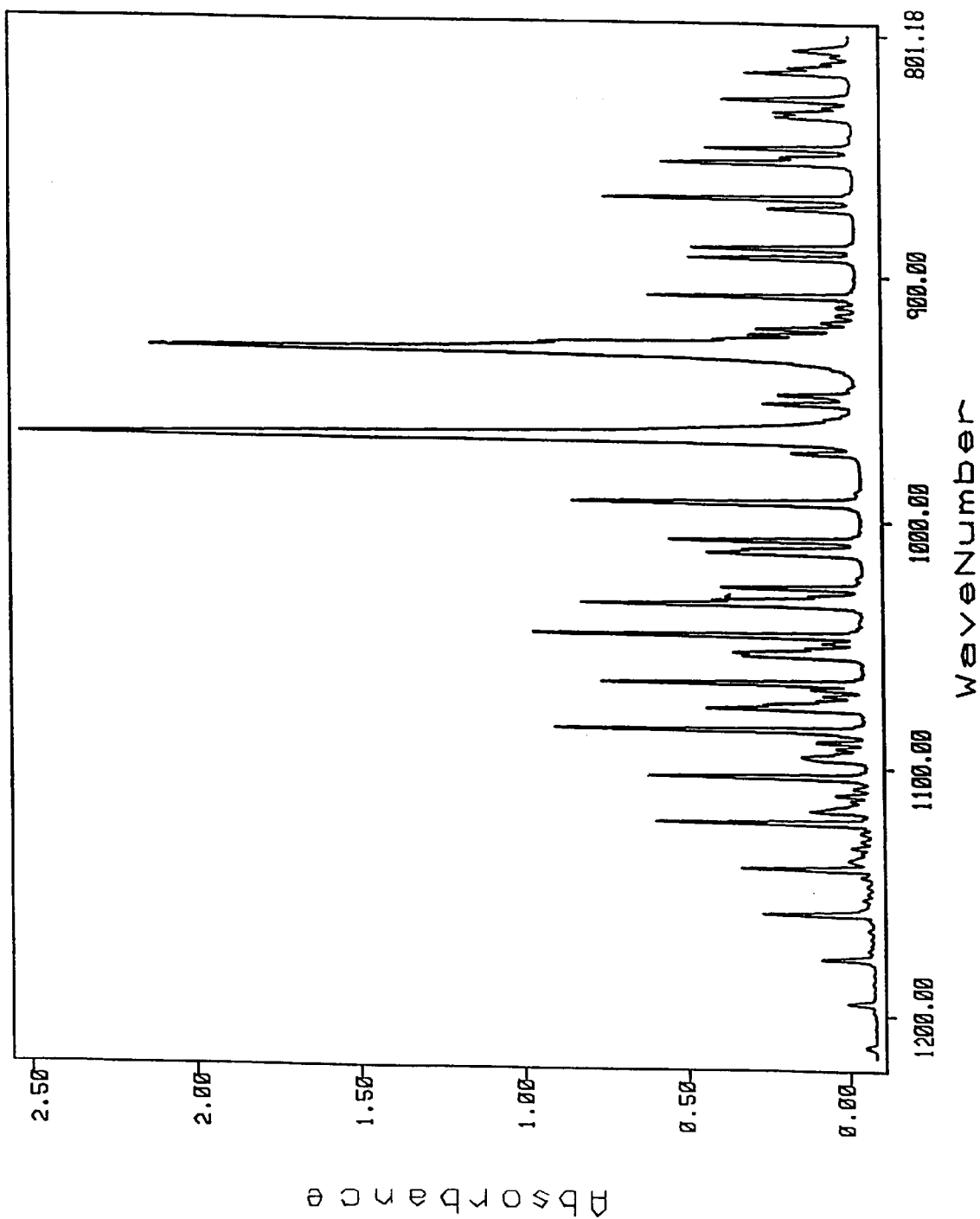
Figure 5E:
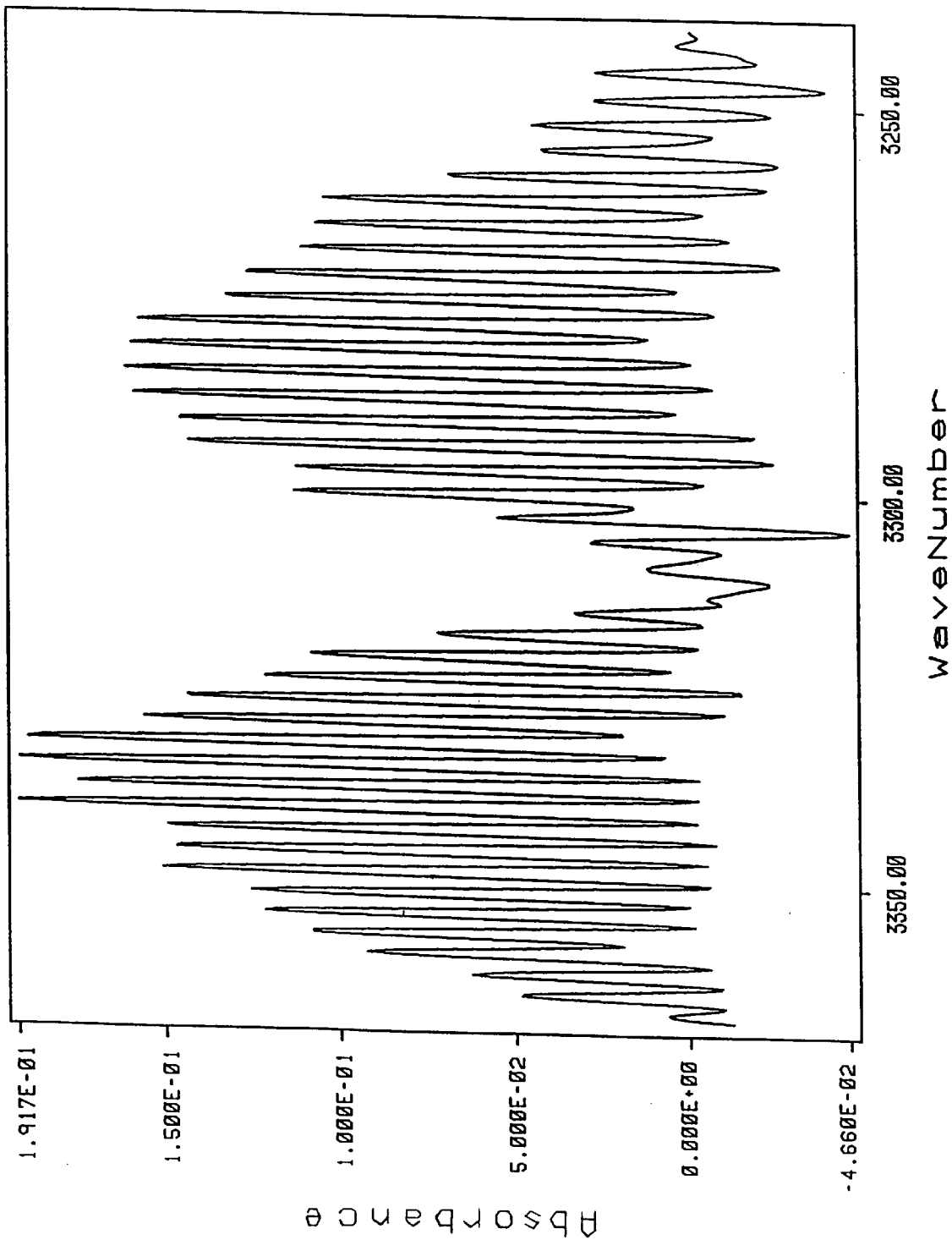
Figure 5F:
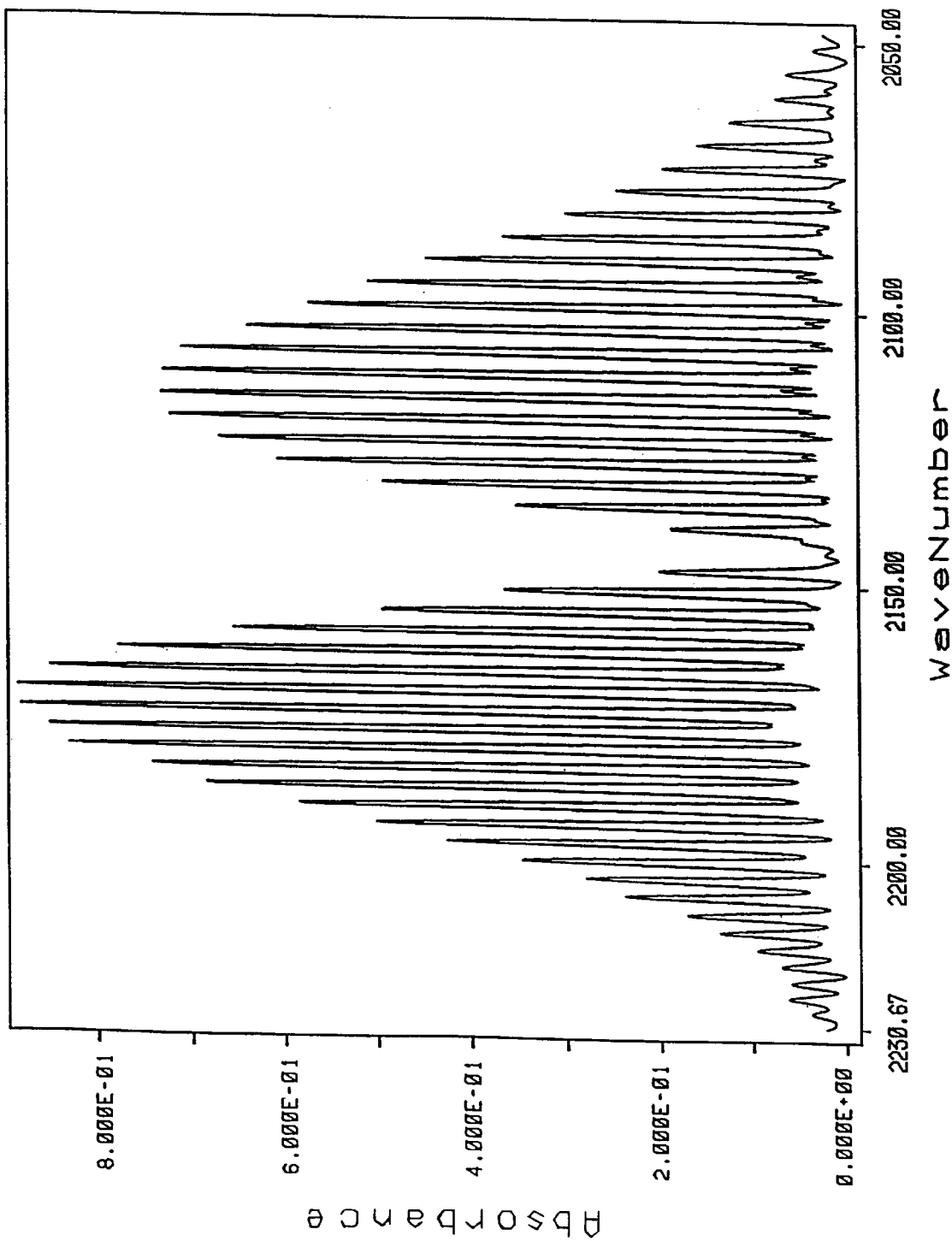
Figure 5G:
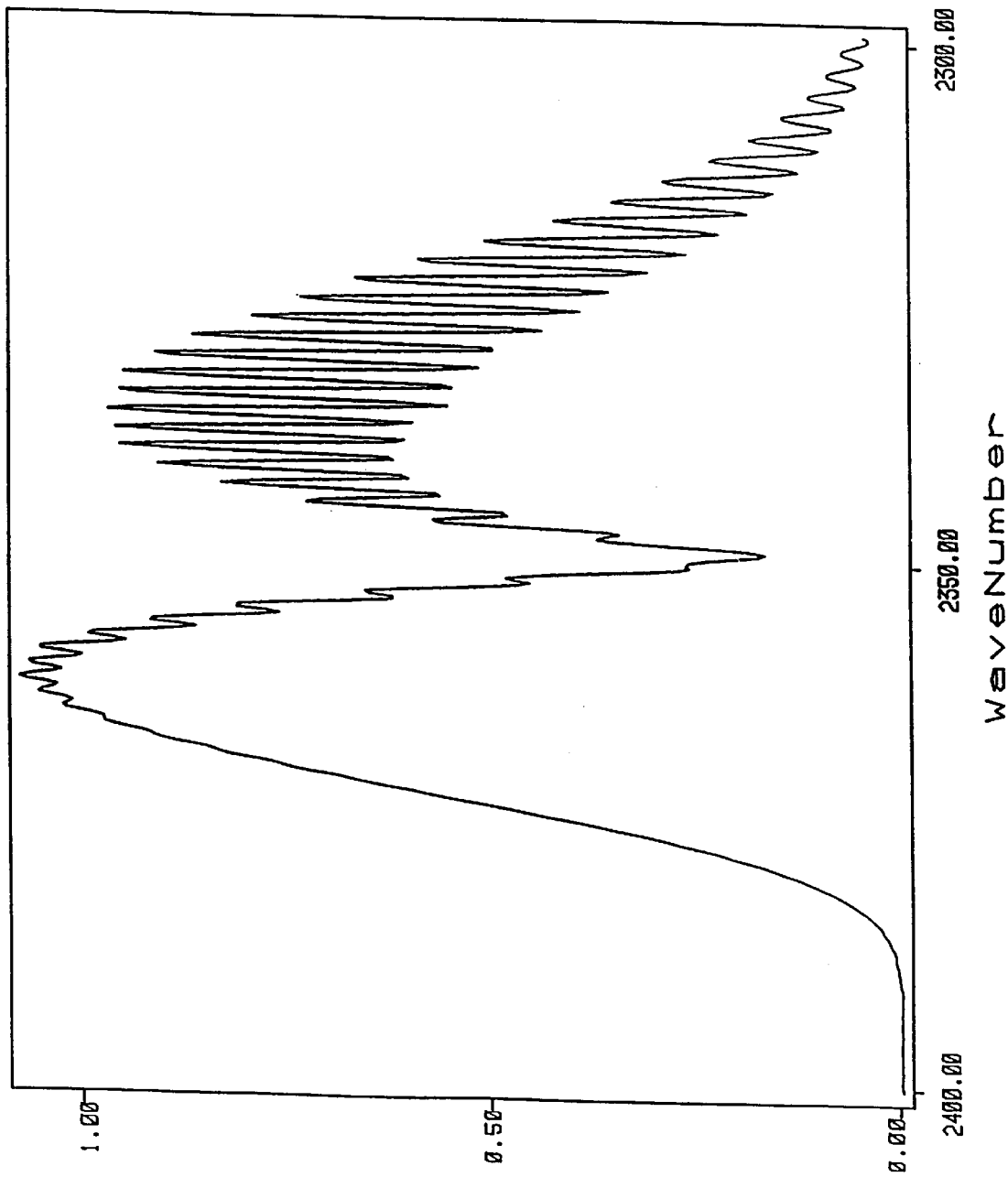
Figure 5H:
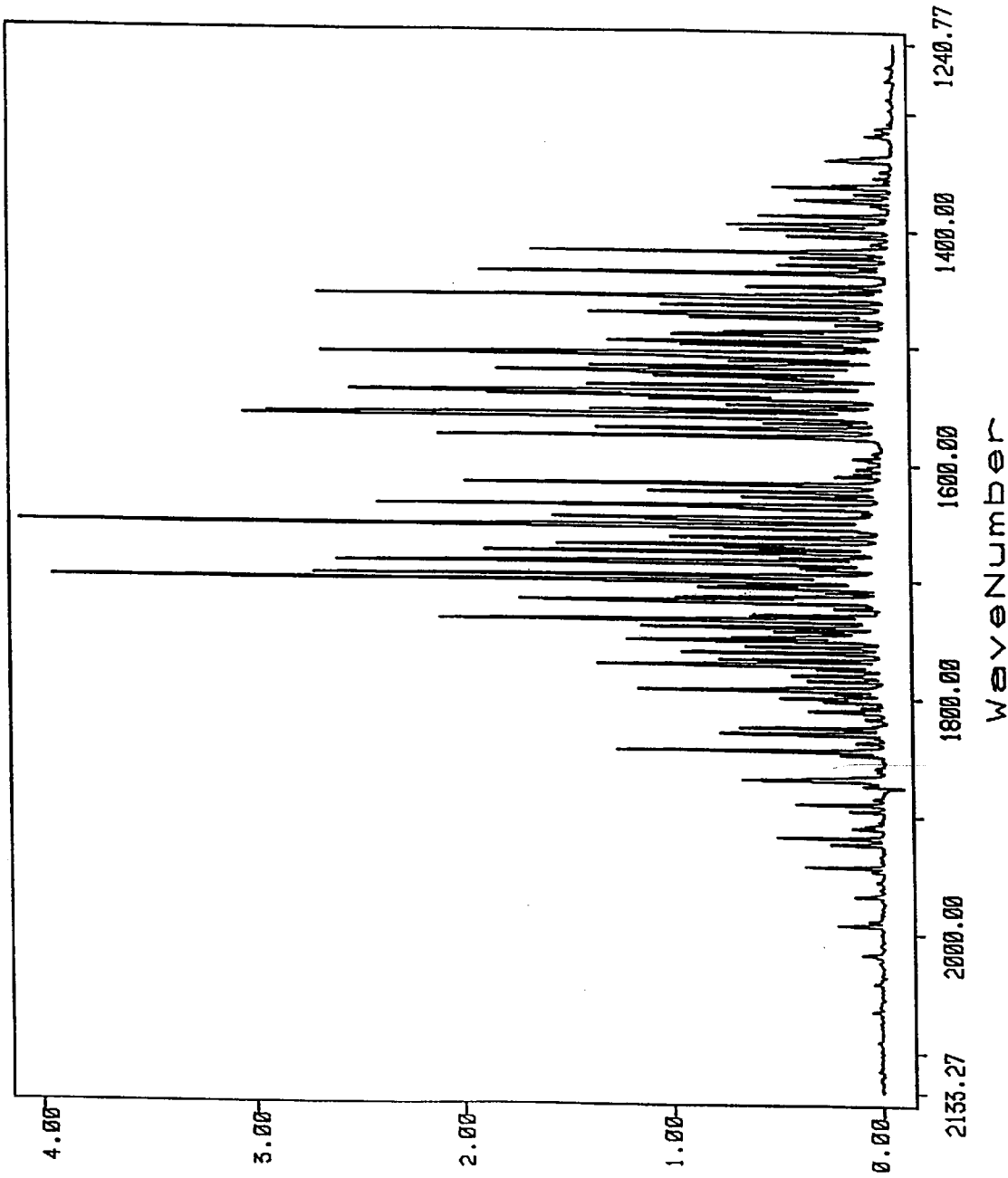
Figure 5I:
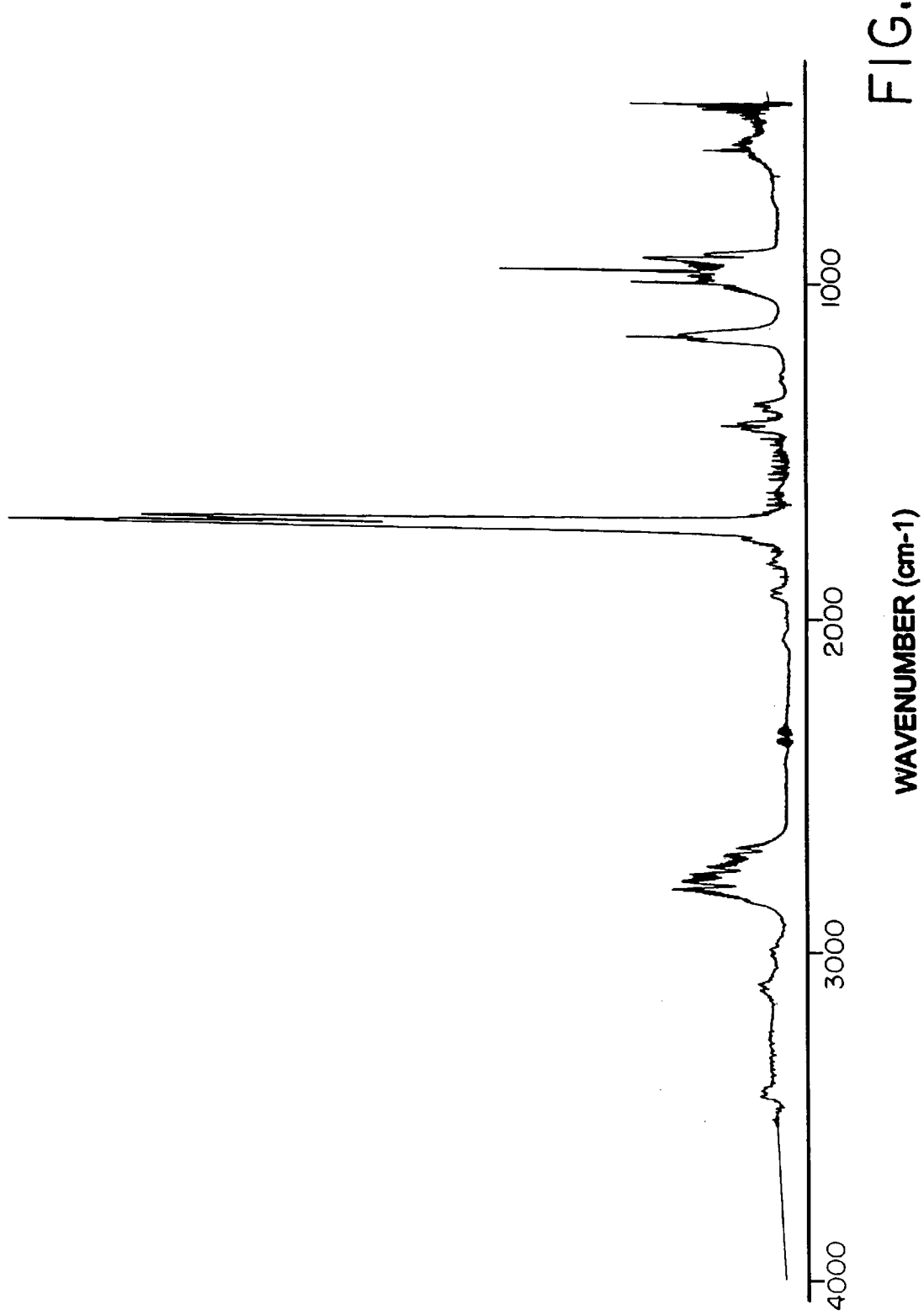
Figure 5J:
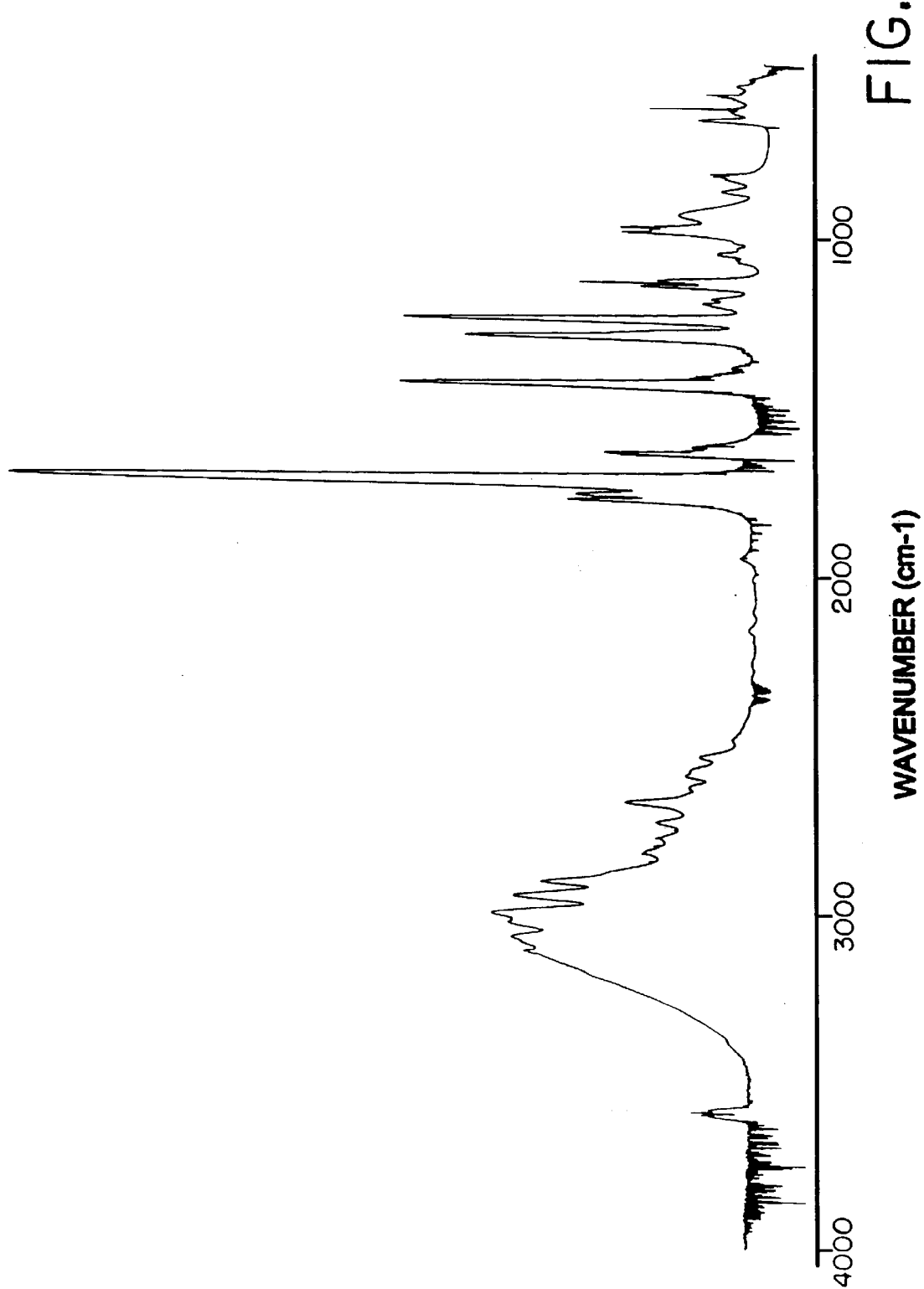

Each of FIGS. 5A–5J is an FT-IR spectrum of one of ten components, of the plurality of components, which are routinely found in measurable and significant quantities in the effluent from an acrylonitrile reactor, collected at room temperature (RT), scaled such that the largest peaks are full scale on the Y-axis, and "smoothed" to reduce the resolution to match that of the spectra of the combined effluent obtained at elevated temperature, such as that shown in FIG. 4. FIG. 5A is an FT-IR spectrum of acrylonitrile (AN) in the region 1200 $cm^{-1}$ to 801 $cm^{-1}$. FIG. 5B is an FT-IR spectrum of acetonitrile in the region 1200 $cm^{-1}$ to 801 $cm^{-1}$. FIG. 5C is an FT-IR spectrum of propylene (Pro) in the region 1200 $cm^{-1}$ to 801 $cm^{-1}$. FIG. 5D is an FT-IR spectrum of ammonia ($NH_3$) in the region 1200 $cm^{-1}$ to 801 $cm^{-1}$. FIG. 5E is an FT-IR spectrum of hydrogen cyanide (HCN) in the region 3350 $cm^{-1}$ to 3250 $cm^{-1}$. FIG. 5F is an FT-IR spectrum of carbon monoxide (CO) in the region 2230 $cm^{-1}$ to 2050 $cm^{-1}$. FIG. 5G is an FT-IR spectrum of carbon dioxide ($CO_2$) in the region 2400 $cm^{-1}$ to 2300 $cm^{-1}$. FIG. 5H is an FT-IR spectrum of water ($H_2O$) in the region 2133 $cm^{-1}$ to 1241 $cm^{-1}$. FIG. 5I is an FT-IR spectrum of acrolein (Aln) in the region 3500 $cm^{-1}$ to 801 $cm^{-1}$. FIG. 5J is an FT-IR spectrum of acrylic acid (AA) in the region 4000 $cm^{-1}$ to 801 $cm^{-1}$.

The spectra of each of the ten components were collected at RT, while the spectra of the combined effluent of the acrylonitrile reactor were collected at approximately 200° C. The separate spectra of these ten components are shown for exemplary purposes. The peaks of each of the ten components present in the combined effluent from the acrylonitrile reactor appear in the spectrum thereof, although the peaks may overlap with those due to other components and may be slightly shifted in wavenumber due to the temperature difference. For this and other reasons, the calibration curves for the present invention should be obtained using the combined effluent, and recovery run analyses on the combined effluent, rather than by attempting to obtain calibration curves based on spectra for each individual component.

The FT-IR spectra shown in FIGS. 4 and 5A–5J were collected by means of a BOMEM Michelson FT-IR spectrometer, as shown schematically in FIG. 1 and described above. The effluent, or a portion thereof, from the acrylonitrile reactor is plumbed to the FT-IR sample cell 36 mounted in the BOMEM Michelson FT-IR spectrometer. The output from the spectrometer 48 is sent to the microprocessor 50 on which is loaded dedicated software, such as the CAAP software from BOMEM, described below. For preparation of calibration curves, at the same time the FT-IR data is being collected, a sample of the effluent is collected for recovery run analysis. In general, a plurality of FT-IR spectra are collected for each recovery run sample collected, when data is being collected for preparing calibration curves.

Identification and Quantitative Calibration Procedures

The dedicated software used in developing the present invention is the BOMEM Continuous Automated Analysis Program (CAAP). The BOMEM CAAP software is designed for use with the BOMEM FT-IR spectrometer used herein. The BOMEM CAAP software is used in obtaining calibration data and calibration curves, and in adaptation of the BOMEM FT-IR spectrometer system to the uses described herein. A program was written using CAAP software, which records and saves the spectra of the effluent passing through the FT-IR sample cell. The program makes use of the CAAP software, but works within it, much like a macro in a spreadsheet or word processing program.

In developing calibration curves for the present invention, a total of 420 FT-IR spectra were recorded and grouped into 42 groups of 10 spectra each. Each of the ten spectra in a group corresponds to one recovery run analysis. Each set of ten spectra was recorded over a period of 24 minutes, during which time the recovery run sample was continuously collected. Of the 42 spectra, 38 spectra actually corresponded to separate recovery run samples, duplicate groups of spectra having been recorded for some effluent samples, for which only single recovery run samples were collected.

Each FT-IR spectrum in each set of ten such spectra is examined for the presence of anomalous noise, unexpected signals, evidence of analyzer problems, and consistency between the ten spectra. One spectrum is selected as representative. In the absence of some indication of defect in the spectra, the fifth spectrum in the series of ten is generally selected to be used for development of the calibration equations or curves. Thus, the calibration set described as an example herein consisted of 38 spectra and 38 associated sets of recovery run analytical results.

A partial least squares (PLS) analysis may be used to examine both absorption band variables and concentration data variables. PLS extracts components called factors directly relevant to both sets of variables. These components are extracted in decreasing order of relevance. PLS actually uses the concentration information during the decomposition process to assist in identifying relevant absorption bands. Spectra containing higher constituent values are weighted more heavily than those with low values. This process generates one set of vectors and corresponding scores for the spectral data, and one set of vectors and corresponding scores for the component concentrations. The two sets of scores are regressed and a correlation vector obtained, which is referred to herein as the calibration curve for the components in the effluent and the associated FT-IR spectral data.

In order to cross-validate the method and resulting calibration curves, approximately 30% of the spectra and associated recovery run results are left out of the calibration procedure, and are later analyzed. Where the data or the calibration curves herein are stated to have been validated, the procedure includes withholding approximately 30% of the FT-IR data and associated recovery run data from the calculation, determining the calibration curves, and then the withheld data are integrated one by one and the calibrations redetermined. The process of redetermining calibration curves while withholding other data is repeated while the other data is withheld, and so on. This procedure minimizes the possibility of developing models based on correlations between mole % data and random variations in the FT-IR spectra which are not associated with changes in concentration of the particular species under analysis for development of a calibration curve. In addition to the foregoing validation procedure, the standard error of calibration and cross-validation may be calculated.

During development of the present invention, occasional shifts in the baseline of the FT-IR spectra were observed. In order to cancel the effects of such baseline shifts, in every spectrum, immediately after measurement every spectrum is baseline corrected by subtracting the absorbance value at 2523 cm$^{-1}$ from every absorbance data point in the spectrum. This correction was programmed and has been used for every measurement in the examples set forth herein. This correction should be made in spectra obtained according to the present invention. This correction eliminates any effect of baseline shift from the quantitative values calculated from the spectra, in both the calibration and the operational samples.

The results of the validation procedures and calculations of standard error and cross-validation show that the calibration curve closely tracks the actual concentration of the plurality of components in the effluent from the acrylonitrile reactor as provided by standard laboratory recovery run analyses. The major difference between these techniques is that the FT-IR data collection and calculation of concentrations of the components in the effluent from the acrylonitrile reactor provides immediate, real-time information on the concentrations of the components, whereas the recovery run analysis requires many hours to provide the same quantitative results. Because of the temporal limitations of recovery run analysis, it cannot provide the real-time information needed to control the operation of an acrylonitrile reactor in real-time. Thus, the techniques of FT-IR and computer analysis from calibration curves provides timely information which can be used to immediately control and optimize the operation of the acrylonitrile reactor in real-time.

The following Table shows, for each of ten individual components which may be present in the effluent from an acrylonitrile reactor, the spectral regions, in cm$^{-1}$, and the standard error of validation (SEV), obtained from an exemplary calibration procedure.

TABLE 1

| COMPONENT | SPECTRAL REGION, cm$^{-1}$ | SEV |
| --- | --- | --- |
| Acrylonitrile | 780–900 | 0.15 |
|  | 992–1200 |  |
|  | 1850–2000 |  |
| Propylene | 800–920 | 0.03 |
| Ammonia | 844–850 | 0.18 |
| Carbon Dioxide | 2241–2299 | 0.11 |
| Carbon Monoxide | 2156–2200 | 0.06 |
| Hydrogen Cyanide | 3252–3285 | 0.04 |
| Water | 1960–1975 | 0.25 |
| Acetonitrile | 800–1500 | 0.02 |
| Acrolein | 1658–1750 | 0.015 |
| Acrylic Acid | 1140–1180 | 0.014 |

The SEV is calculated from the following equation:

$$SEV = \sqrt{\frac{\sum_{i=1}^{n}(Yk_i - Yp_i)^2}{n}}$$

Where Yk is the recovery run concentration, $Y_p$ is the concentration using the FTIR model, and n is the number of samples in the set of FTIR spectra and recovery run samples. As described herein, the value of $Y_p$ for a particular sample was calculated by using a model developed without that sample in the set, a process known as cross-validation, and the SEV is sometimes referred to as standard error of cross-validation.

Figure 6A:
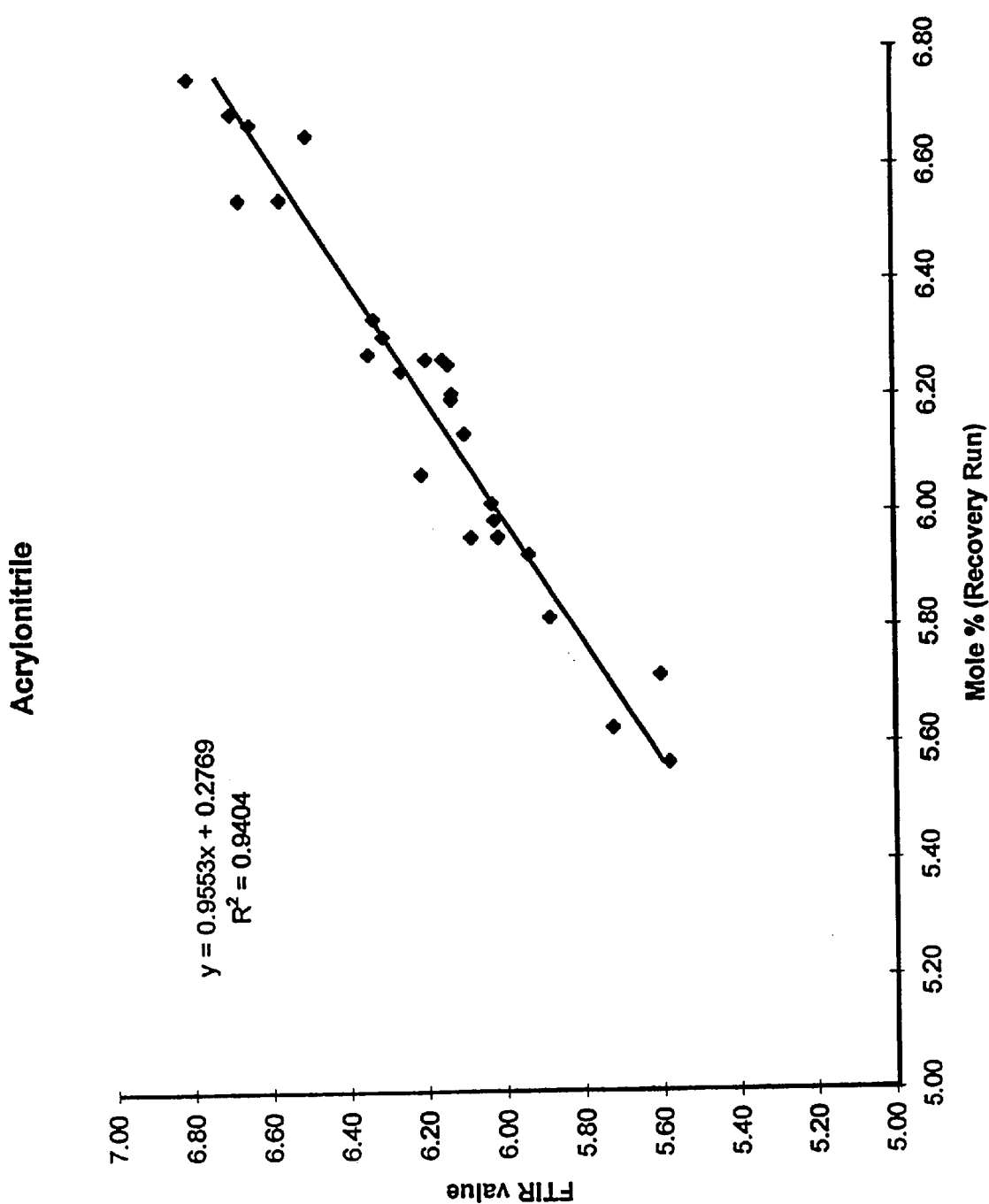
FIGS. 6A–6J are graphs of FT-IR mole % value vs. recovery run mole % values for ten individual components of an effluent of an acrylonitrile reactor in which propylene is the hydrocarbon feed, in which the FT-IR data has been validated, each graph showing the values for an individual component.
Figure 6B:
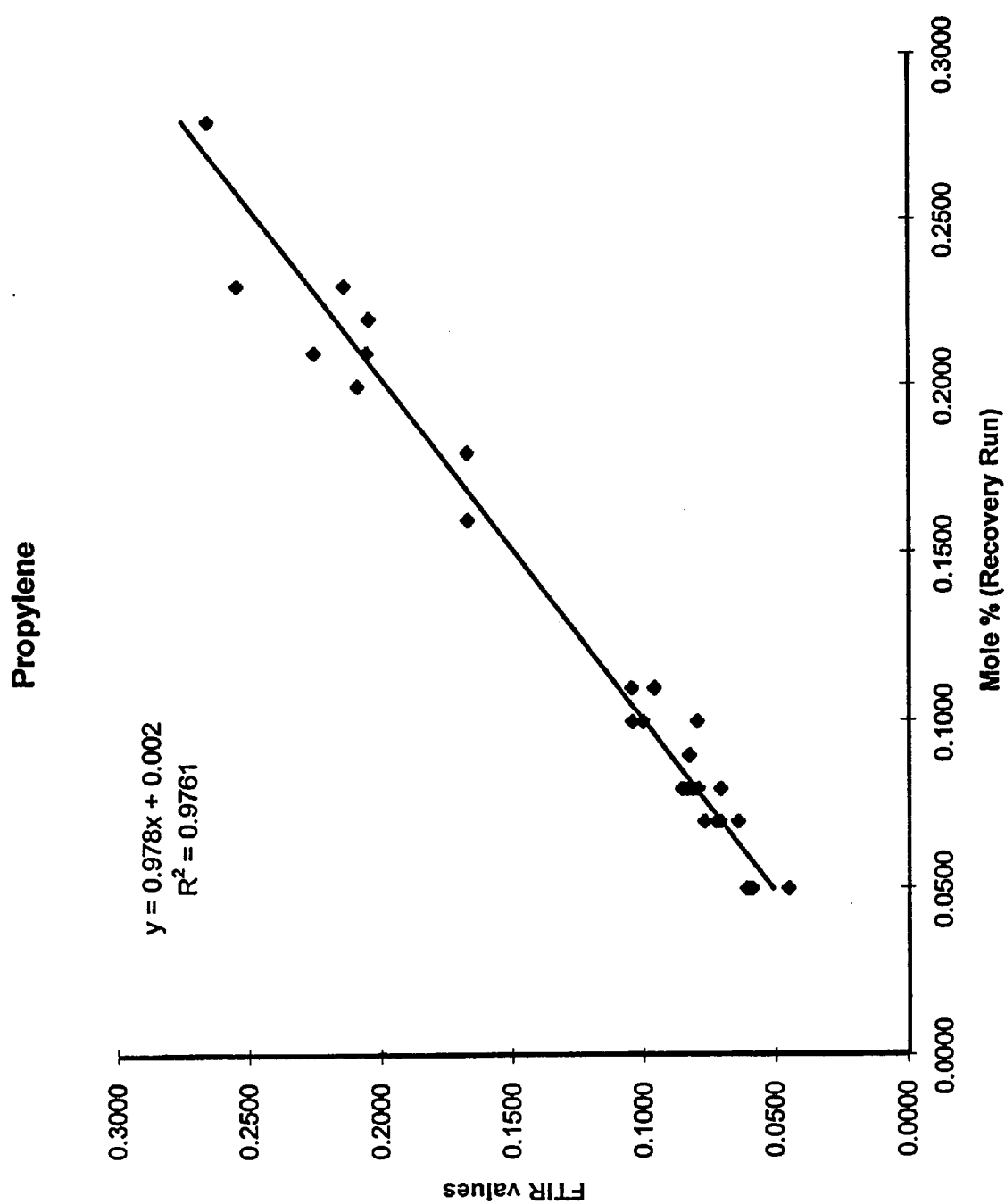
Figure 6C:
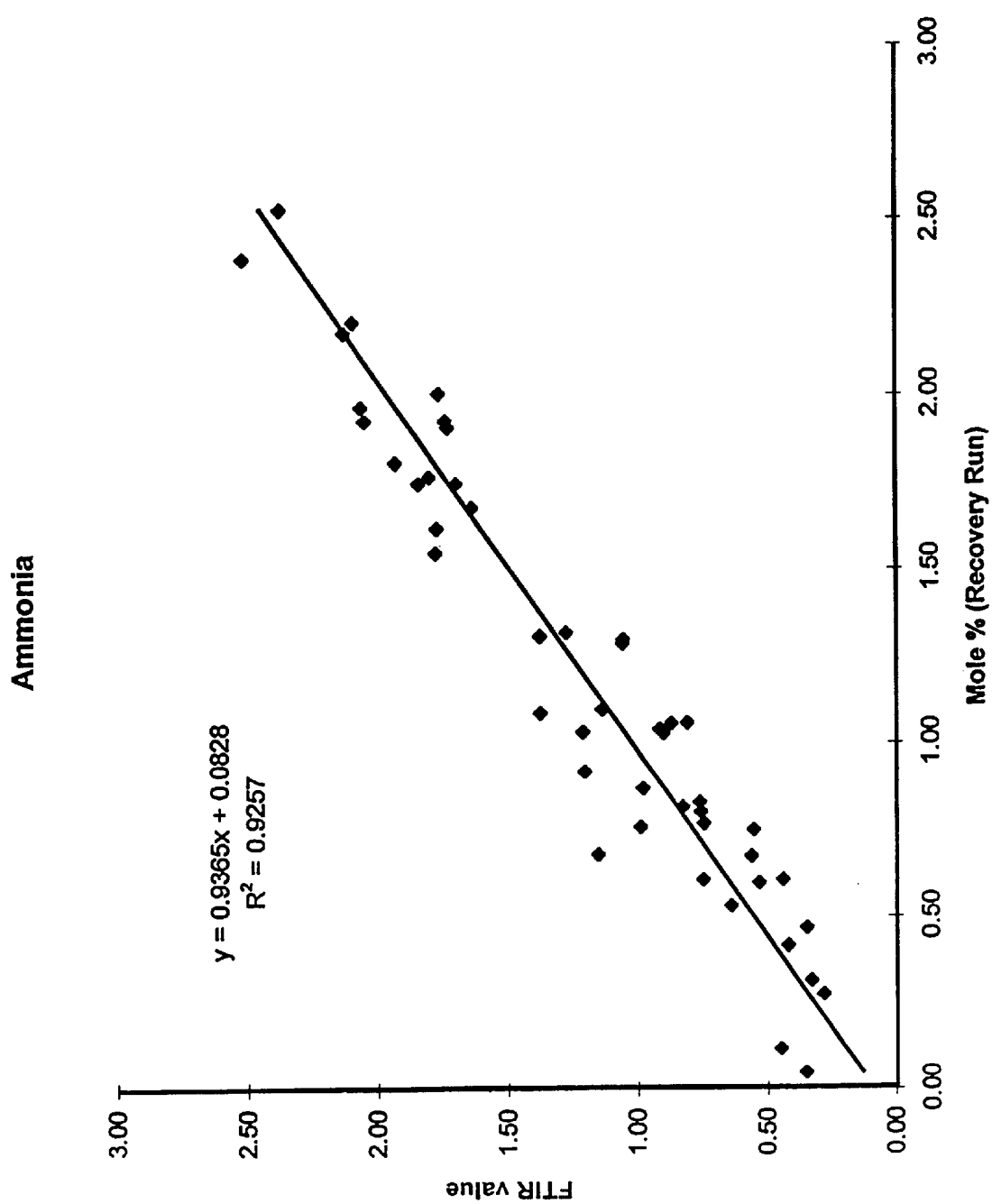
Figure 6D:
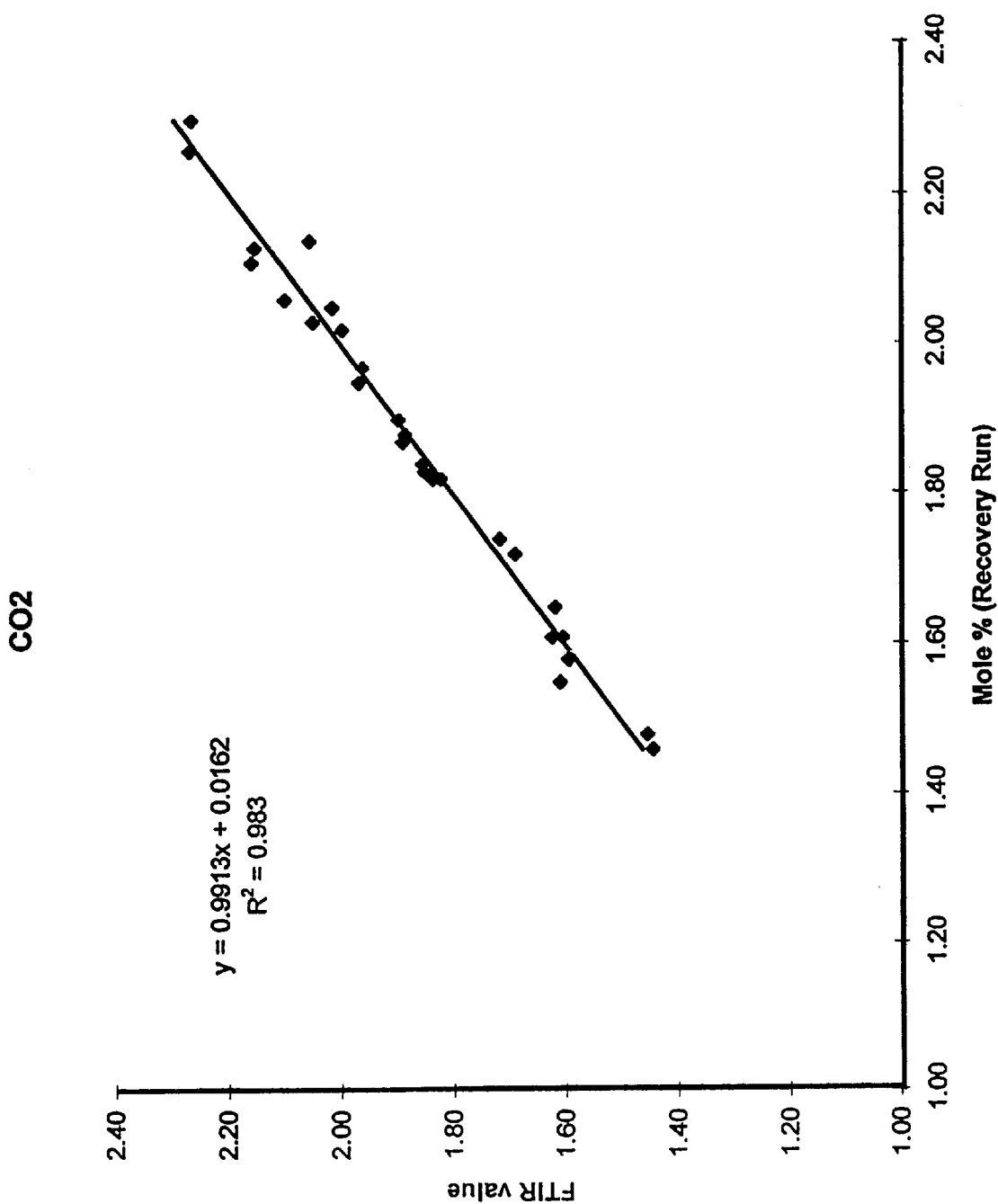
Figure 6E:
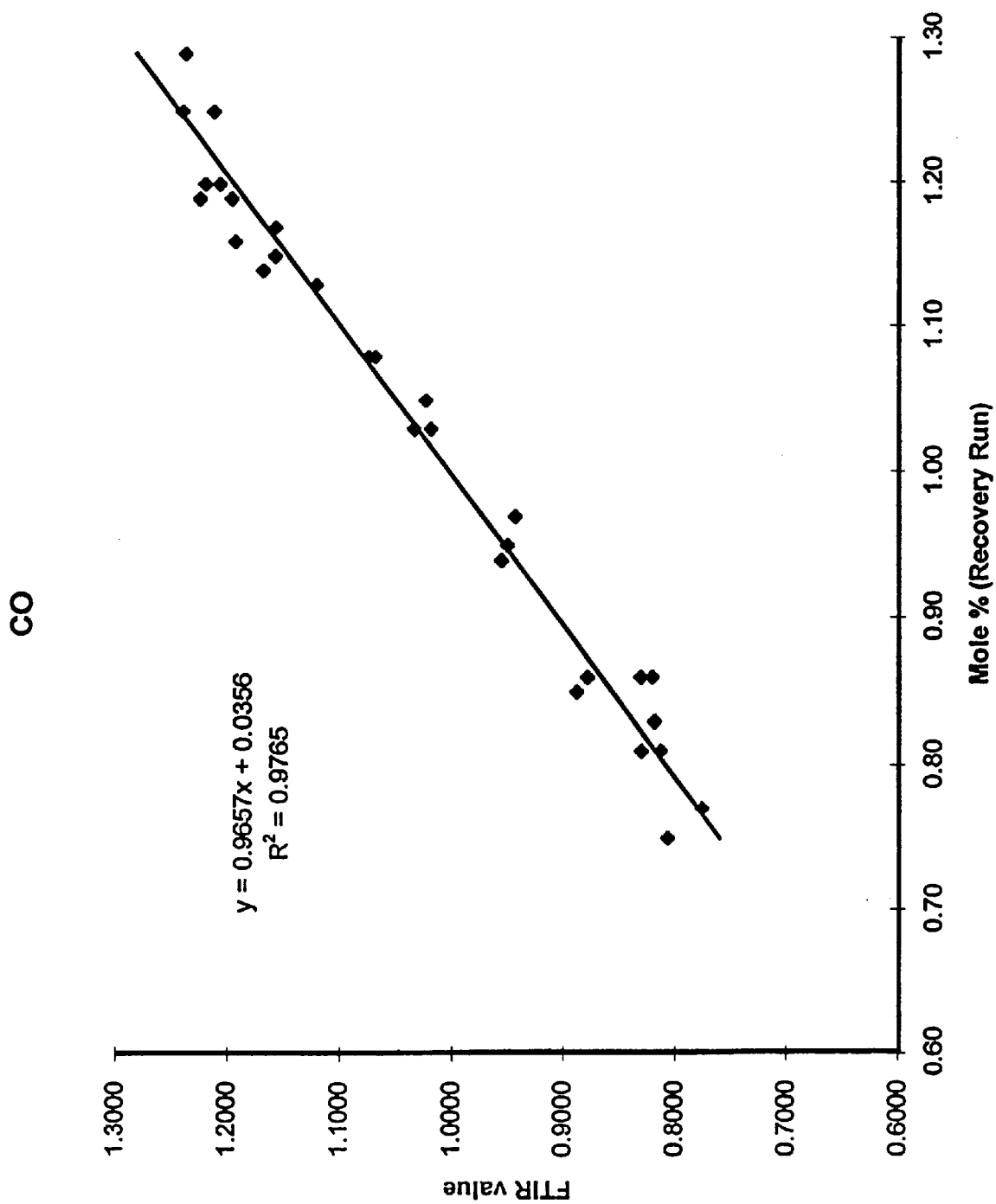
Figure 6F:
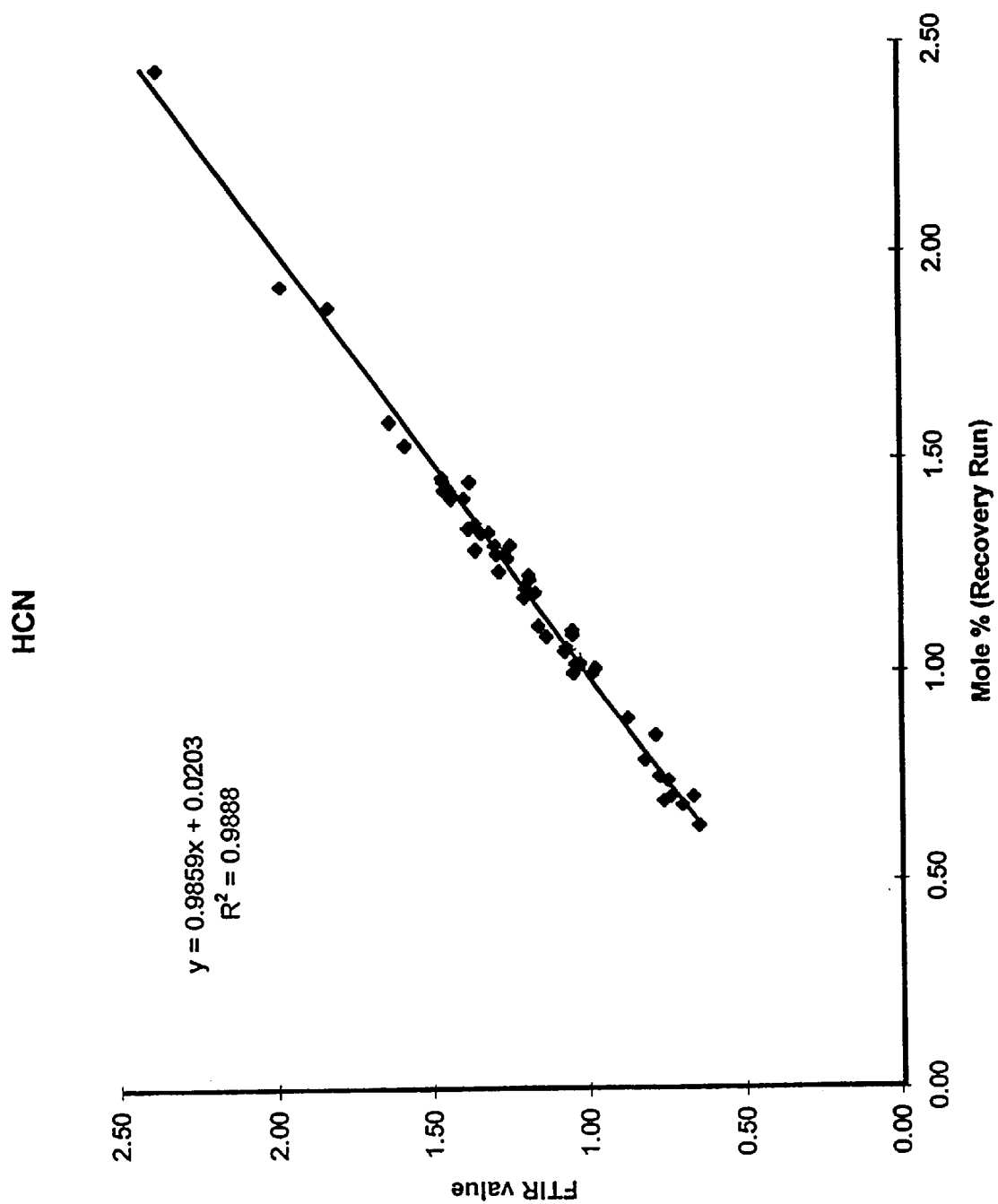
Figure 6G:
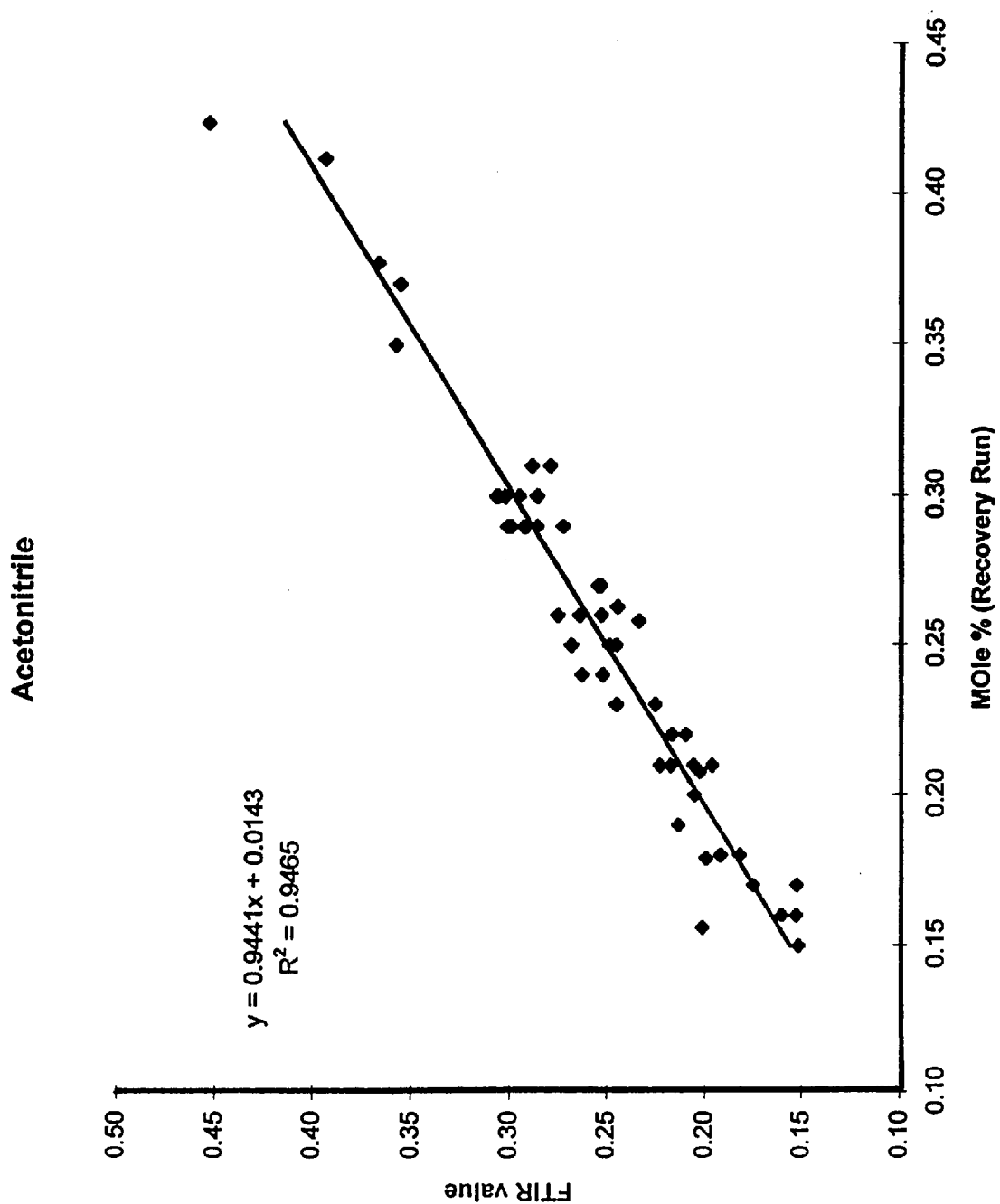
Figure 6H:
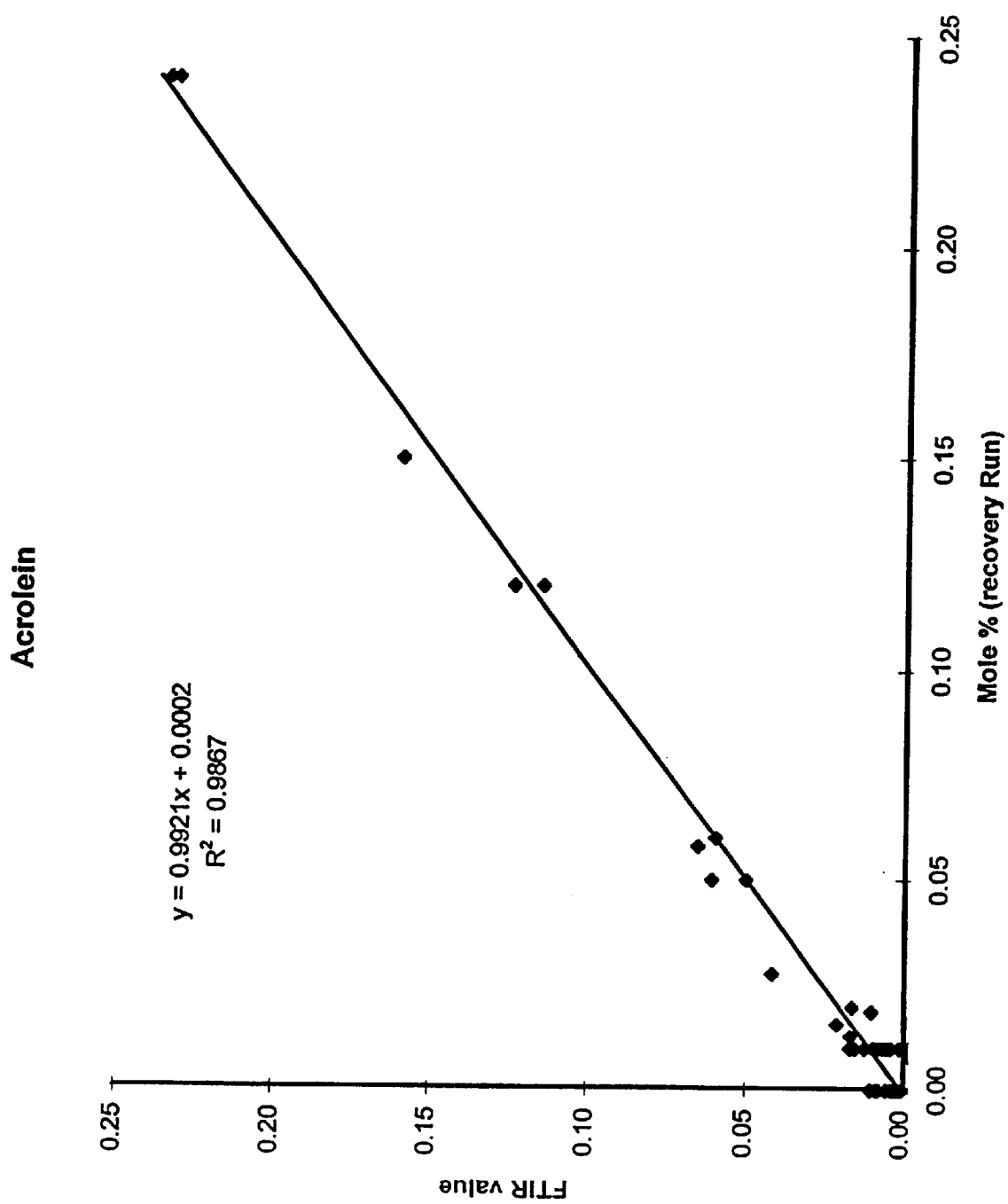
Figure 6I:
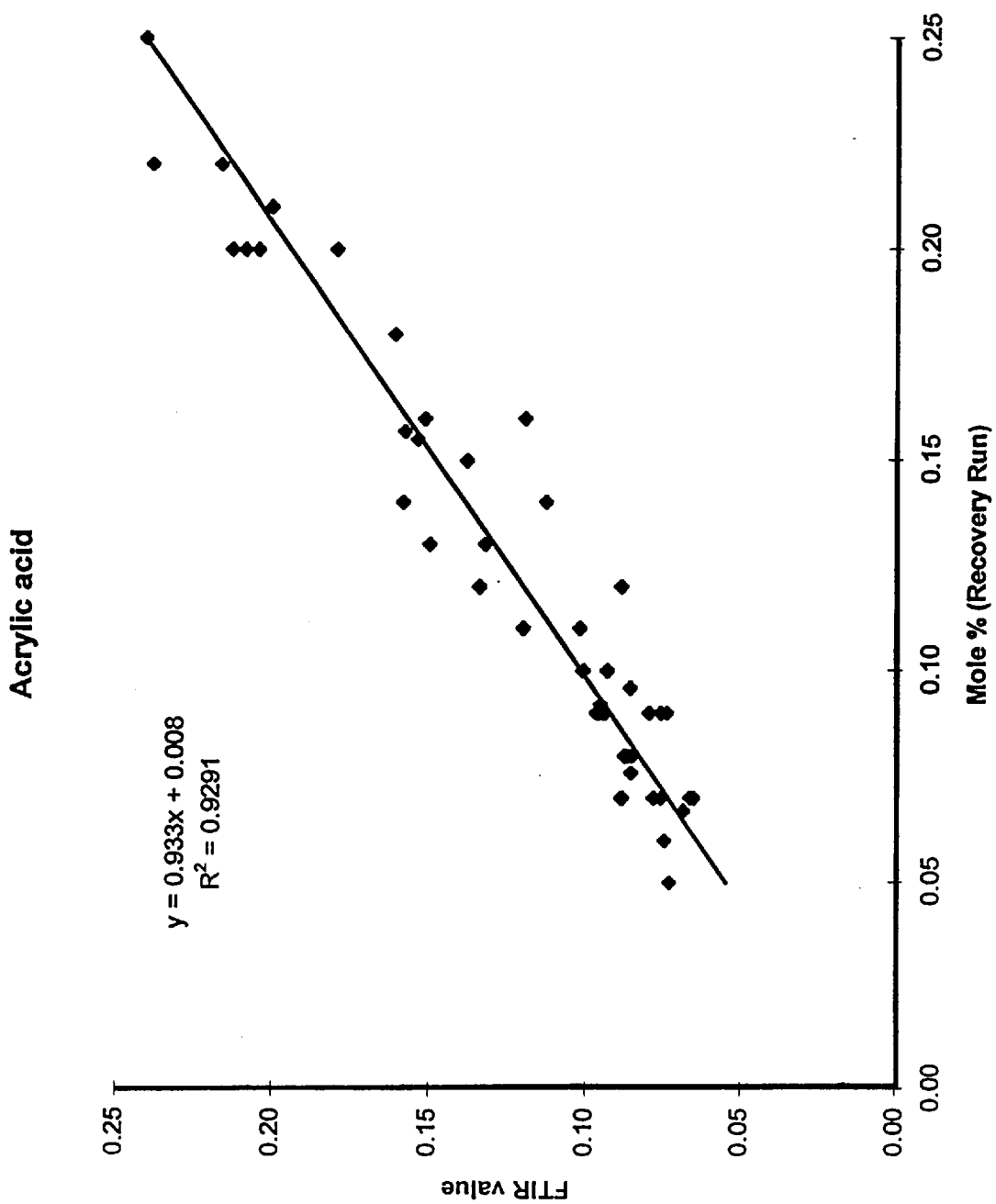
Figure 6J:
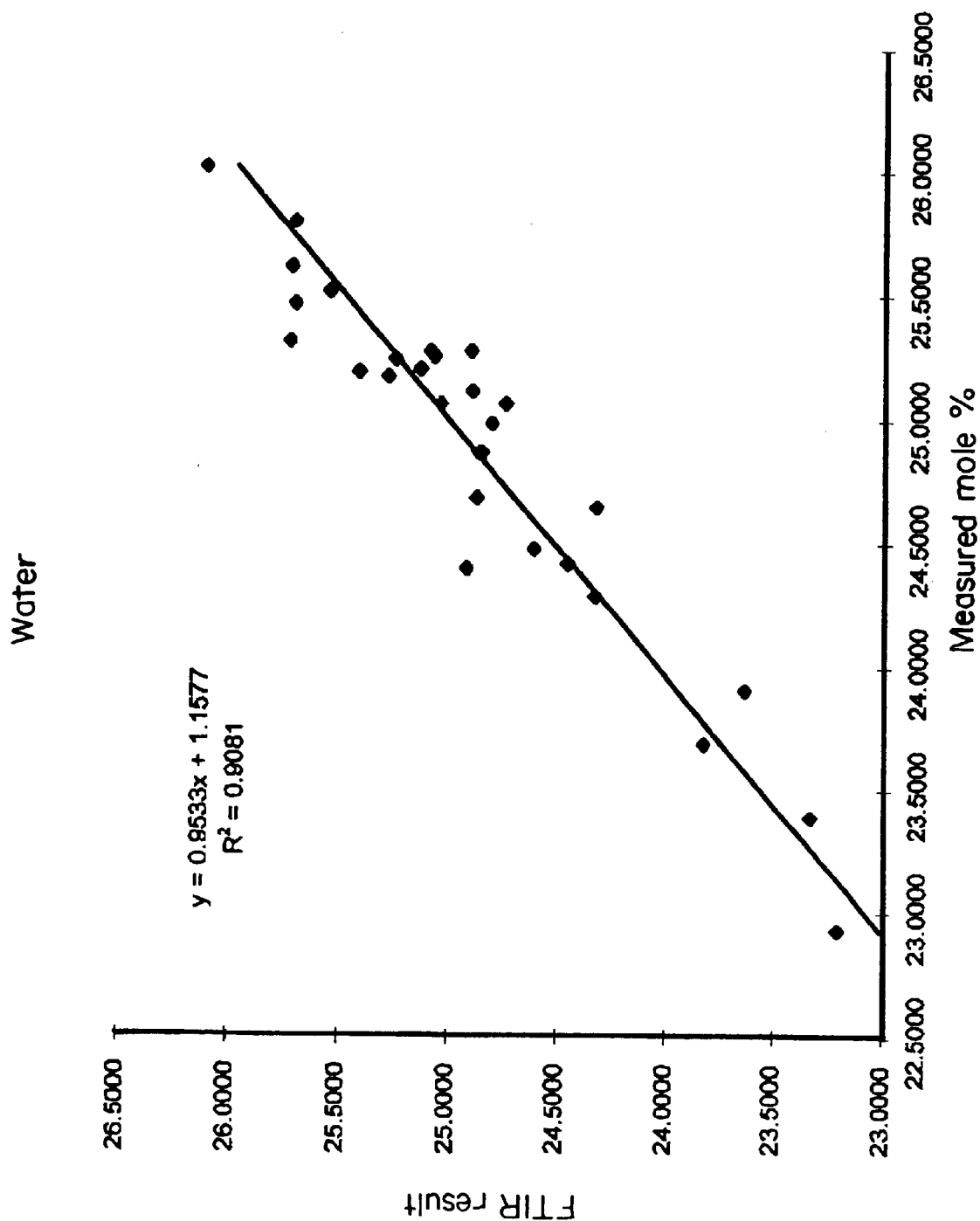

FIGS. 6A–6J are graphs of FT-IR mole % value vs. mole % values obtained from recovery run analyses, for ten components of an effluent of an acrylonitrile reactor in which propylene is the hydrocarbon feed. For each graph, the validated FT-IR mole % values are plotted against measured mole % values obtained from recovery run analyses. FIGS. 6A–6J are representative of the calibration curves which are used by the microprocessor of the present invention to calculate the content of each of the components in the effluent from an acrylonitrile reactor. The graph shown in FIG. 6A is a calibration curve for acrylonitrile and is shown with the equation for the line and the value for the correlation coefficient, R$^2$, obtained the data upon which the graph is based. The graph shown in FIG. 6B is a calibration curve for propylene and is shown with the equation for the line and the value for the correlation coefficient, R$^2$, obtained the data upon which the graph is based. The graph shown in FIG. 6C is a calibration curve for ammonia (NH$_3$) and is shown with the equation for the line and the value for the correlation coefficient, R$^2$, obtained the data upon which the graph is based. The graph shown in FIG. 6D is a calibration curve for carbon dioxide (CO$_2$) and is shown with the equation for the line and the value for the correlation coefficient, R$^2$, obtained the data upon which the graph is based. The graph shown in FIG. 6E is a calibration curve for carbon monoxide (CO) and is shown with the equation for the line and the value for the correlation coefficient, R$^2$, obtained the data upon which the graph is based. The graph shown in FIG. 6F is a calibration curve for hydrogen cyanide (HCN) and is shown with the equation for the line and the value for the correlation coefficient, R$^2$, obtained the data upon which the graph is based. The graph shown in FIG. 6G is a calibration curve for acetonitrile and is shown with the equation for the line and the value for the correlation coefficient, R$^2$, obtained the data upon which the graph is based. The graph shown in FIG. 6H is a calibration curve for acrolein and is shown with the equation for the line and the value for the correlation coefficient, $R^2$, obtained the data upon which the graph is based. The graph shown in FIG. 6I is a calibration curve for acrylic acid and is shown with the equation for the line and the value for the correlation coefficient, $R^2$, obtained the data upon which the graph is based. The graph shown in FIG. 6J is a calibration curve for water ($H_2O$) and is shown with the equation for the line and the value for the correlation coefficient, $R^2$, obtained the data upon which the graph is based.

Figure 7:
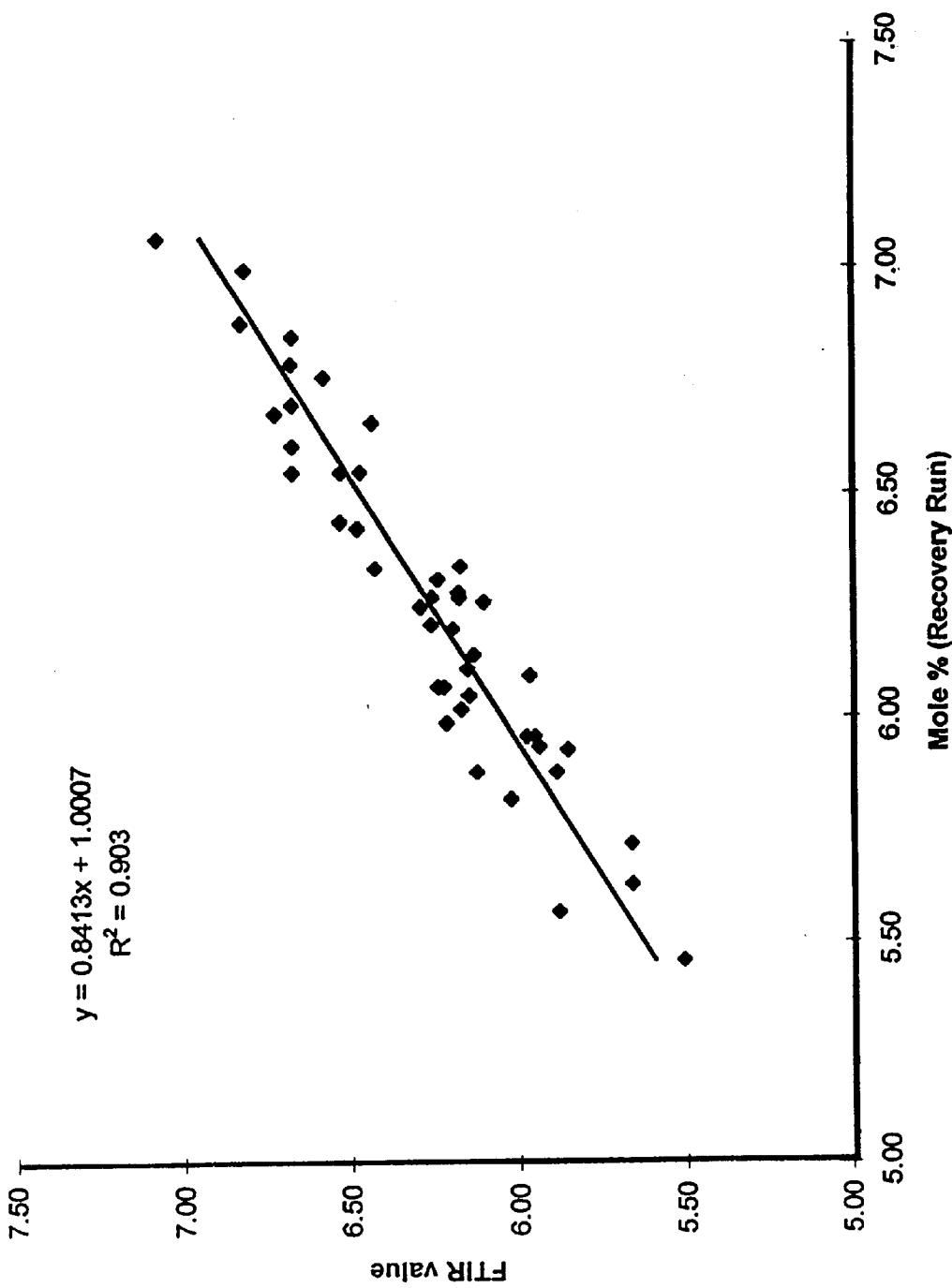
FIG. 7 is a graph of FT-IR mole % value vs. recovery run mole % values for acrylonitrile from the effluents of two different acrylonitrile reactors in each of which different grades of propylene were the hydrocarbon feed, based on recovery run analyses performed by different analysts in different laboratories, and in which the FT-IR mole % was obtained on different FT-IT spectrometers.

FIG. 7 is a graph of FT-IR mole % value vs. recovery run mole % values for acrylonitrile from the effluents of two different acrylonitrile reactors in each of which different grades of propylene were the hydrocarbon feed. The graph in FIG. 7 is based on recovery run analyses performed separately on the effluents of the two acrylonitrile reactors, by different analysts in different laboratories, and by using separate FT-IR instruments on the effluents of the two acrylonitrile reactors. The FT-IR data in each case has been validated by the procedure set forth above. In addition to the graph, the equation for the line and the value for the correlation coefficient, $R^2$, obtained for the data upon which the graph is based are shown. The data were recorded over a long period of time in order to test both the calibration procedure and the long-term stability and reproducibility of the method. The feed gases were of widely varying quality during the time period in which this data was collected. This experiment was conducted to assure that the calibration model developed would include all possible variability. This graph shows the robustness of the method of the present invention.

Figure 8:
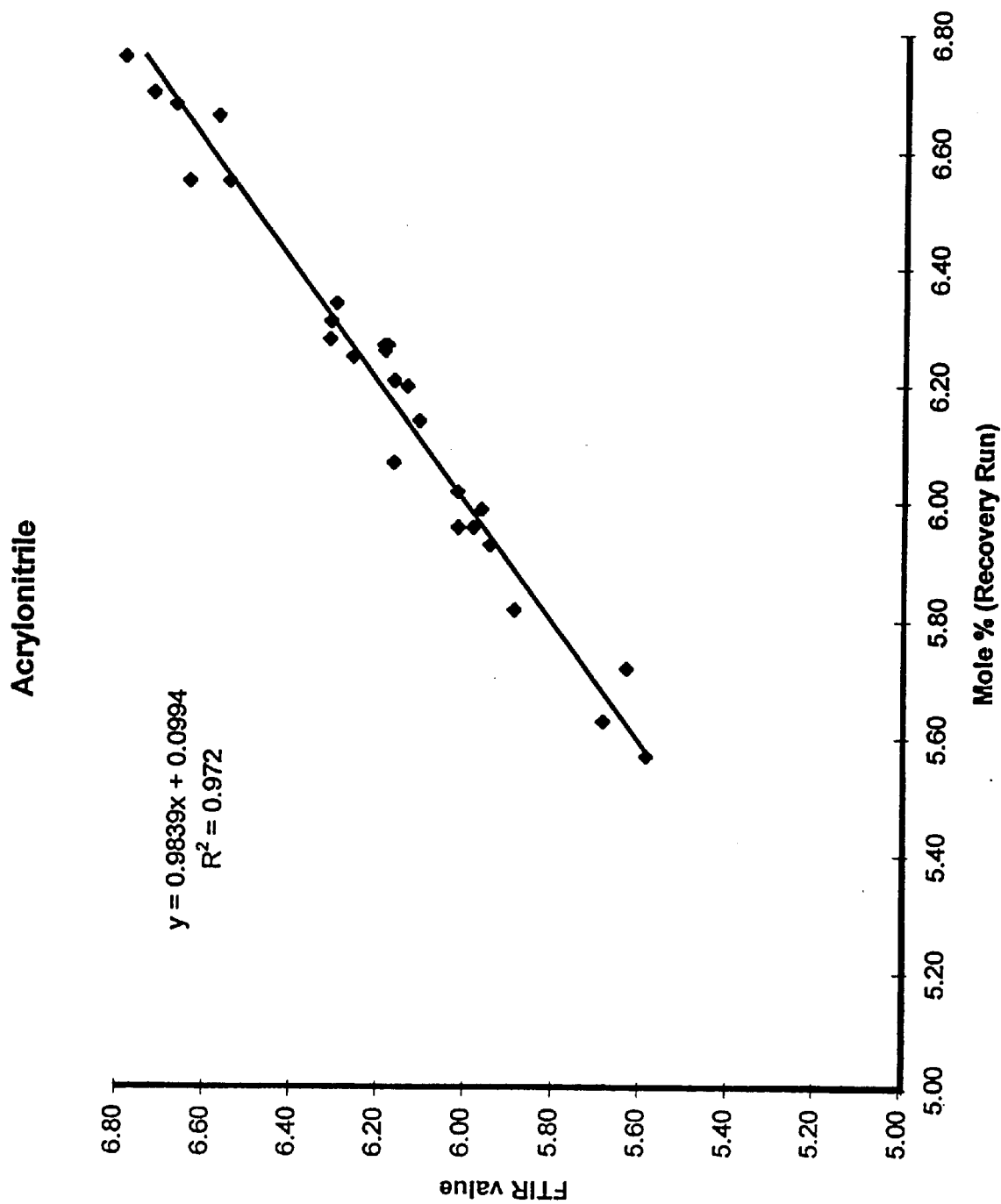
FIG. 8 is a graph of FT-IR mole % value vs. recovery run mole % values for acrylonitrile from an effluent of an acrylonitrile reactor in which propylene is the hydrocarbon feed, in which the model is used on all data from FT-IR mole % values and all data from recovery run mole % values.

FIG. 8 is a graph of FT-IR mole % value vs. recovery run mole % values for acrylonitrile from an effluent of an acrylonitrile reactor in which propylene is the hydrocarbon feed, in which the model is used on all data from FT-IR mole % values and all data from recovery run mole % values, and is shown with the equation for the line and the value for the correlation coefficient, $R^2$, obtained the data upon which the graph is based. In this graph, all available FT-IR data was used to determine the FT-IR mole % data from the available acrylonitrile calibration curves, and was plotted against the recovery run mole % data for the corresponding samples collected contemporaneously with the respective FT-IR data. This graph shows, for acrylonitrile, that excellent correlation results can be expected between FT-IR mole % data obtained by the method of the present invention, based on comparison of the FT-IR mole % data with the recovery run mole % data.

The pressure in the FT-IR cell may affect the calibration and the resulting analyses. The FT-IR cell has a constant volume and is generally held at a constant temperature. An increase in internal the pressure in the FT-IR cell thus correlates to a greater number of molecules of the components of the effluent from the acrylonitrile reactor being in the FT-IR cell. Changes in pressure result in broadening of peaks in the spectra recorded by the FT-IR spectrometer. The peaks may be further distorted due to differential broadening of individual peaks, since the effects of pressure are likely different on different bonds in different molecules, the vibration of which gives rise to the IR absorptions. For these reasons, it is important to operate the FT-IR sample cell at a constant pressure, and, more importantly, the pressure in the FT-IR sample cell during an operating period should be the same pressure used to develop the calibration curve data used for that equipment.

Detailed Statistical Calibration Procedures

Partial Least Square (PLS) is a technique for quantitative analysis which has been applied to spectroscopic and chromatographic data. The technique ultimately is applied to Beer's Law, shown in the following equation:

$$A_1 = C_1 K_1$$

where $A_1$ is the absorbance at a given wavelength or wavenumber, $C_1$ is the concentration of the component giving rise to the absorbance, and $K_1$ is the absorptivity constant for the component. Using Beer's law, one can calculate the absorptivity of a component with a known concentration, then by simply measuring the absorbance and using the calculated absorptivity constant, calculate the concentration of an unknown sample containing the component of interest. PLS assumes some linear relationship between the measurement and the concentration of a particular component, although the technique allows use of many different wavelengths to be used as factors in applying Beer's Law. For a mixture containing two components, Beer's Law can be written for each component:

$$A_1 = C_1 K_1 + E_1$$

$$A_2 = C_2 K_2 + E_2$$

where $E_1$ and $E_2$ are the residual errors normally due to the instrument and sample handling. Provided there is no relationship between the two absorbances ($A_1$ and $A_2$), then one can solve each equation independently. Since Beer's Law is additive, these equations can be solved simultaneously and hence handle the case where there is some interference within a single spectrum between the two absorbances:

$$A_1 = C_1 K_{11} + C_2 K_{21} E_1$$

$$A_2 = C_1 K_{12} + C_2 K_{22} E_2$$

When more than one component is involved, matrix methods can be used. In matrix terms the above equations can be written as:

$$A_{(n,p)} = C_{(n,m)} K_{(m,p)} + E_{(n,p)}$$

where n is the number of calibration samples, p is the number of wavelengths, and m is the number of components. In matrix notation, the above equation can be written:

$$A = CK + E$$

Using computers, the equations for the matrix of absorptivity coefficient and the best least squares line fit to the data can be obtained. Once these equations are solved for the K matrix, the K matrix can be used to predict concentration of unknowns. This method of quantitative analysis is known as the K matrix or the Classical Least Squares (CLS) method.

If the concentration of one or more components are unknown, then solving for the K absorptivity coefficients will have some significant error. One way to resolve this is to rearrange Beer's Law and write concentration as a function of absorbance:

$$C = AP + E$$

For a mixture containing two components the equation can be written as:

$$C_1 = A_1 P_{11} + A_2 P_{12} E_1$$

$$C_2 = A_2 P_{21} + A_2 P_{22} E_2$$

Using the above equations, the absorptivity constant (P) can be calculated even when the concentration of the second component is unknown. Writing concentration as a function of absorbance and solving for the P matrix is known as the P matrix or the Inverse Least Squares (ILS) method.

The PLS algorithm is derived from the CLS and ILS methods, and has similarity to an algorithm known as PCR. The PLS and PCR algorithms and their general goals are similar to the CLS and ILS methods. In the example of a mixture with two components, there are ideally two independent variables in the system. That means that the spectra of the mixture can be reconstructed by adding together the spectra of pure component A and pure component B. In reality, particularly in the case of IR, this is not so simple. Usually there are some instrument or sample variations or some interaction between pure components A and B which produces some intermediate component or simple changes such as the shape of the bands or the baseline of the spectrum. But even in a system as complex as an IR spectrum, there are a finite number of independently varying spectra that, when added together, will reconstruct the spectrum of the mixture. In PLS and PCR terms, Beer's Law can be written:

$$A=TB+E$$

where B is the number of the independently varying spectra known as the loading vectors or loadings factor and T is the amount of each spectrum that should be added to reconstruct the spectrum of the original mixture and is known as the score. Generally, the amount of each spectrum depends on the concentration of the components. This process reduces the complexity and one can use a small number of loadings to reconstruct or model the spectra of unknowns. Since the same loadings are always used to model the unknown, the only differences in the spectra of different component concentrations is the amount of each loadings or the scores. Since the scores are unique to the concentration of each individual component and the training spectrum, then the absorbance term can be replaced by scores in both CLS and ILS equations.

In order to create a simplified representation of data, i.e., scores and loadings, spectral decomposition has been used. This process is also known as Principal Component Analysis (PCA) and it proceeds as follow:

1. Calculate the average of all the training (calibration) spectra.
2. Compare each spectrum in the training set to the average spectrum and calculate the variances between them. This is the first loading vector.
3. Calculate the amount of loading vector in each spectrum in the training set. This value is the score.
4. Calculate the contribution of the loading (loading vector times the score) for each spectrum in the training set and subtract this from each training spectrum.
5. Use the resultant training data and substitute it for the original data. Then step 1 to 5 is repeated for each individual training samples.

The calculated scores are used to perform ILS to calculate the concentration for each training sample. Performing PCA or spectral decomposition to obtain a reduced representation of the data and performing regression to obtain the calibration matrix is known as the PCR algorithm.

PLS is related to PCR and both use spectral decomposition. However, the main difference between the two techniques is how the decomposition step is preformed. In PCR, the spectra are decomposed based on the maximum variances between the data. In PLS, the spectral decomposition is weighted according to the concentrations. This means that the absorption bands with higher values are weighted more heavily than those with the lower values. Thus, the loading vectors calculated using PLS are quite different from the PCR loading vectors.

In PLS and PCR, the data compression step is achieved by retaining only the part of the information which is significant and discarding noise (or unrelated information). Generally, the significant information part is assumed to lie within the first few factors and the noise portion is restricted to the remainder of the factors. The user has to decide what number of factors are essential for the calibration. One way of selecting the optimum number of factors is by using the PRESS criterion as outlined in the following.

Determining the number of factors to use in PLS or PCR model is the most important step in building a model. A balance must be obtained by using sufficient factors to describe significant variances in the data set but not using too many factors and overfitting the model.

One way to determine the optimum number of factors is by evaluating the PRESS (Predicted Residual Error Sum of Squares) values. PRESS is calculated as follows:

1. Leave one of the samples in the training set out use the remainder to perform the decomposition step, and obtain the calibration matrix.
2. Predict the concentration of the sample that has been left out by using the calibration matrix.
3. Calculate the difference between the predicted concentration and the actual. This is a single PRESS value.
4. Now include back the sample that was left out previously and leave another sample out and predict the concentration using one factor. Calculate the square sum of residual and add this to the previous PRESS.
5. Repeat step 1 to 4 for all the set factors in the calibration.

Another way to determine the optimum number of factors is to calculate the standard error of prediction (SEP). SEP is defined as the $$SEP=[(\Sigma d^2-N*D^2)/N-1]^{1/2}$$

Where d is the difference between the predicted and actual values; D is the mean of the difference between the predicted and actual values, and N is the number of samples in the training set. The SEV provides an overall estimate of the quality of the correlation, and provides a guide for use in selection of the number of factors (i.e., IR absorption bands) to use in the PLS analysis.

In the ideal case, both PRESS and SEP values should be at their maximum within the first few factors, then they should decrease, reach a minimum, and then increase again. Theoretically, the point where PRESS and SEP reach their minimum is the optimum number of factors for the model.

In PLS there is generally three types of outliers, as follows:

(a) spectra which differ from those of other samples in the training set, such as spectra with poorly resolved or anomalous absorption bands;
(b) spectra of samples with erroneous concentration values, such as from contaminated samples;
(c) spectra of samples with concentration values quite different from those of other samples.

Outliers of type (a) and (b) are due to instrumental errors and poor sample handling techniques. Once these types are identified as outliers, they should be discarded from the calibration model. Outliers of type (c) are also known as "unique" samples. These types of samples are unique because of their concentration values, either too high or too low in comparison to the rest of the samples in the training set. The absence of more samples with concentrations at the same level makes these samples stand out from the rest and they are labeled "unique". Whether these samples are included depends on a number of factors. Of particular concern is whether such values are expected during the operation of the system for which the calibration is prepared. It is important to recognize and differentiate such unique samples from those of type (a) and (b). A problem may arise if a unique sample is included in the calibration set which may more properly be a type (a) or (b) outlier. In such a case, a false calibration range might be obtained, if such a sample is not within the range of the samples from the system under study. For example, consider a calibration set with 10 samples having concentrations ranging from 2 to 15 units. If a sample having a concentration value of 30 is included in the final calibration set, and the correct calibration range should have been 2 to 15 units, the calibration range actually obtained will be 2 to 30 units. In such case, results falling in the 15 to 30 range may not be accurate.

The calibration data handling procedure, including preparation of the calibration curve may be performed in a microprocessor. In one embodiment, the microprocessor is programmed to calculate calibration data for and to quantify each of the components in the effluent from an acrylonitrile reactor. In one embodiment, the microprocessor is programmed to output the quantitative results for each of the plurality of components. In one embodiment, the quantitative data is output to a reactor controller communicating with the acrylonitrile reactor. In one embodiment, the reactor controller is adapted to adjust and control operation of the acrylonitrile reactor based on the quantitative data. In one embodiment, the reactor controller is controlled by a microprocessor programmed to control and optimize the acrylonitrile reactor based on the quantitative data derived from the FT-IR. In one embodiment, the microprocessor which controls the reactor controller is the same microprocessor which is programmed to calibrate and quantify each of the components in the effluent from the acrylonitrile reactor. In one embodiment, the microprocessor which controls the reactor controller is a different microprocessor, and the microprocessor is programmed to control the reactor controller, and to thereby control and optimize the acrylonitrile reactor.

The following Table 2 includes exemplary results which may be obtained by the system of the present invention. The data shown in Table 2 represent three test runs, in which the apparatus and methods of the present invention were employed to control and optimize the operation of an acrylonitrile reactor based upon real-time quantitative analysis of the components in an effluent stream from the reactor. In performing the experimental methods described herein, the apparatus as described herein was used. The apparatus included a microprocessor and a FT-IR spectrometer, where the microprocessor was programmed to identify and quantify each of the plurality of components based upon absorbance data obtained by the FT-IR spectrometer, and upon calibration data obtained from recovery run analyses in the FT-IR sample cell.

For each of the experiments, a calibration curve was used for each of the plurality of components which had been previously prepared as described herein. For each of the experiments, initial real-time FT-IR absorbance data was obtained for the operational effluent from the acrylonitrile reactor before control by the microprocessor and reactor controller was initiated. The initial FT-IR absorbance data was used to calculate the conversion and yield, as shown in the "BEFORE" columns in Table 2. The initial FT-IR absorbance data was input to the microprocessor which calculated real-time quantitative data for the operational effluent from the FT-IR absorbance data and the calibration curves for the components. Control of the reactor was then transferred to the microprocessor and reactor controller which was then allowed to control the operation of the acrylonitrile reactor to optimize production of the acrylonitrile component based on the quantitative data. The resulting absorbance data for the optimized operational effluent is shown in the "AFTER" columns in Table 2. As a confirmation of the quantitative data obtained by the method of the present invention shown in the AFTER column, the data shown in the "RECOVERY RUN" columns in Table 2 was obtained by standard chemical, recovery run, analysis. As is shown, the method of the present invention provides excellent results by controlling, and thereby optimizing, operation of the acrylonitrile reactor. As is shown by the recovery run results, the real-time results for conversion and yield obtained by the FT-IR and microprocessor agrees quite well with the results obtained by the more time-consuming chemical recovery run analyses.

TABLE 2

| | BEFORE | | AFTER | | RECOVERY RUN | |
| --- | --- | --- | --- | --- | --- | --- |
| Example | Conversion | Yield | Conversion | Yield | Conversion | Yield |
| 1 | 73.123 | 56.443 | 98.5 | 73.51 | 97.57 | 75.31 |
| 2 | 78.864 | 62.886 | 98.5 | 77.89 | 98.31 | 78.40 |
| 3 | 65.204 | 49.601 | 98.5 | 73.40 | 98.66 | 75.05 |

While the invention has been described in conjunction with specific embodiments herein, it is evident that many alternatives, modifications and variations will be apparent to those skilled in the art in light of the foregoing description. Accordingly it is intended to embrace all such alternatives and modifications in variations as for within the spirit and broad scope of the appended claims.

What is claimed is:

1. An apparatus for identifying and quantifying a plurality of components in an effluent stream from an ammoxidation reactor, comprising:

an ammoxidation reactor having an outlet connected to an effluent line which contains said effluent stream;

a microprocessor; and a Fourier Transform infrared spectrometer connected to said effluent line and having a sample cell through which flows a portion of said effluent stream, an infrared source to emit infrared radiation and pass said infrared radiation through said effluent stream, an infrared detector to detect transmitted infrared radiation at selected infrared wavelengths and to generate absorbance data due to absorbance of said infrared radiation by said components, wherein each of said components absorbs infrared radiation at one or more of said infrared wavelengths, and an output apparatus to provide said absorbance data to said microprocessor;

wherein said microprocessor is programmed to identify and quantify each of said plurality of components based upon said absorbance data and calibration data, said calibration data being obtained from recovery run analysis and calibration analysis in said sample cell;

wherein said effluent stream comprises of acrylonitrile, acetonitrile, propylene, ammonia, hydrogen cyanide, carbon monoxide, carbon dioxide, water, acrolein and acrylic acid as said plurality of components.

2. An apparatus as in claim 1, further comprising a memory device available to the microprocessor for storing said calibration data for each of the plurality of components.

3. An apparatus as in claim 1, further comprising an output device for outputting quantitative data for each of said plurality of components.

4. An apparatus as in claim 3, further comprising a reactor controller communicating with said ammoxidation reactor and said output device and adapted to adjust and control operation of said ammoxidation reactor based on said quantitative data.

5. An apparatus as in claim 4, wherein said reactor controller controls one or more of reactor temperature, reactor internal pressure, feed of air, feed of hydrocarbon and feed of ammonia.

6. An apparatus as in claim 5, wherein said reactor controller is controlled by said microprocessor.

7. An apparatus as in claim 1, further comprising a display for displaying data input to and output from said microprocessor.

8. An apparatus as in claim 2, wherein said calibration data provided to said memory device has been obtained from effluents from said ammoxidation reactor.

9. An apparatus as in claim 1, wherein said ammoxidation reactor is operated to produce acrylonitrile.

10. An apparatus for monitoring and controlling the operation of an ammoxidation reactor, comprising:

an ammoxidation reactor for the production of acrylonitrile;

an effluent stream from the reactor containing a plurality of components comprising acrylonitrile, acetonitrile, propylene, ammonia, hydrogen cyanide, carbon monoxide, carbon dioxide, water, acrolein and acrylic acid;

an effluent line to carry the effluent stream from the ammoxidation reactor;

a Fourier Transform infrared spectrometer disposed in the effluent line, the Fourier Transform infrared spectrometer comprising a sample cell through which may flow a portion of said effluent stream, an infrared source to emit infrared radiation and pass said radiation through the effluent stream, an infrared detector to detect transmitted infrared radiation at selected infrared wavelengths and to generate absorbance data due to absorbance of said infrared radiation by said components, wherein each of said components absorbs infrared radiation at one or more of infrared wavelengths, and an output device capable of outputting said absorbance data to said microprocessor;

a microprocessor in communication with the Fourier Transform infrared spectrometer via a FT-IR output line;

an input device in communication with said microprocessor via an input line;

a reactor controller in communication with said microprocessor via an output line and in communication with said ammoxidation reactor via a reactor control line;

a set of mass flow control valves in communication with said reactor controller, said set of mass control valves comprising: an air control valve; a hydrocarbon control valve; and an ammonia control valve;

a set of reactant feed lines to carry reactants to said ammoxidation reactor, said set of reactant feed lines comprising: a hydrocarbon feed line; an ammonia feed line; and an oxygen feed line.

wherein said microprocessor is programmed to identify and quantify each of said plurality of components based upon said absorbance data and calibration data, said calibration data being obtained from recovery run analysis and calibration analysis in said sample cell.

* * * * *

UNITED STATES PATENT AND TRADEMARK OFFICE
CERTIFICATE OF CORRECTION

PATENT NO. : 6,284,196 B1  Page 1 of 1
DATED : September 4, 2001
INVENTOR(S) : Casal et al.

It is certified that error appears in the above-identified patent and that said Letters Patent is hereby corrected as shown below:

Column 1,
Line 19, "nitrites. This reaction is" should read -- nitriles. This reaction is --.

Column 5,
Line 32, "about 400°C. to about 55°" should read -- about 400°C to about 550° --.

Column 6,
Lines 6 and 7, "the reactor is a fluid bed" should read -- the reactor 10 is a fluid bed --.

Column 14,
Line 32, "$A_1=C_1K_{11}+C_2K_{21}E_1$" should read -- $A_1=C_1K_{11}+C_2K_{21}+E_1$ --.
Line 62, "$C_1=A_1P_{11}+A_2P_{12}E_1$" should read -- $C_1=A_1P_{11}+A_2P_{12}+E_1$ --.
Line 64, "$C_2=A_2P_{21}+A_2P_{22}E_2$" should read -- $C_2=A_2P_{21}+A_2P_{22}+E_2$ --.

Signed and Sealed this

Eleventh Day of April, 2006

JON W. DUDAS
*Director of the United States Patent and Trademark Office*